United States Patent
Waite, II et al.

(10) Patent No.: US 11,684,479 B2
(45) Date of Patent: *Jun. 27, 2023

(54) TIBIAL TRIAL SYSTEM FOR A KNEE PROSTHESIS AND METHOD

(71) Applicant: DePuy Ireland Unlimited Company, Ringaskiddy (IE)

(72) Inventors: David W. Waite, II, Pensacola, FL (US); Aaron J. Matyas, Fort Wayne, IN (US); Duncan G. Young, Yorkshire (GB); Scott M. Thomas, Fort Wayne, IN (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 165 days.

This patent is subject to a terminal disclaimer.

(21) Appl. No.: 17/208,414

(22) Filed: Mar. 22, 2021

(65) Prior Publication Data

US 2021/0205089 A1 Jul. 8, 2021

Related U.S. Application Data

(60) Continuation of application No. 16/390,667, filed on Apr. 22, 2019, now Pat. No. 10,952,863, which is a continuation of application No. 15/866,047, filed on Jan. 9, 2018, now Pat. No. 10,265,183, which is a
(Continued)

(51) Int. Cl.
*A61F 2/38* (2006.01)
*A61F 2/46* (2006.01)

(52) U.S. Cl.
CPC ............ *A61F 2/389* (2013.01); *A61F 2/4684* (2013.01)

(58) Field of Classification Search
CPC ...... A61F 2/3859; A61F 2/3868; A61F 2/389; A61F 2/4684
See application file for complete search history.

(56) References Cited

U.S. PATENT DOCUMENTS

| | | |
|---|---|---|
| 4,135,517 A | 1/1979 | Reale |
| 4,211,228 A | 7/1980 | Cloutier |
| 4,378,607 A | 4/1983 | Wadsworth |

(Continued)

FOREIGN PATENT DOCUMENTS

| | | |
|---|---|---|
| CN | 102740788 A | 10/2012 |
| CN | 103037807 A | 4/2013 |

(Continued)

OTHER PUBLICATIONS

Extended European Search Report, European Application No. 16181964.4-1654 dated Oct. 25, 2016, 8 pages.

(Continued)

*Primary Examiner* — Eric S Gibson
(74) *Attorney, Agent, or Firm* — Barnes & Thornburg LLP

(57) ABSTRACT

An orthopaedic surgical instrument system for use during a surgical procedure to implant an orthopaedic knee prosthesis includes a tibial trial component adapted to be positioned on a surgically-prepared proximal end of a patient's tibia. The tibial trial component has a base plate and a central post extending upwardly from a superior surface of the base plate. A superior surface of the central post has a ramp surface defined therein, with the ramp surface inclining superiorly in the anterior-to-posterior direction.

11 Claims, 14 Drawing Sheets

Related U.S. Application Data division of application No. 14/265,960, filed on Apr. 30, 2014, now Pat. No. 9,861,491.

(56) References Cited

U.S. PATENT DOCUMENTS

| | | |
|---|---|---|
| D269,547 S | 6/1983 | Rosenthal |
| 4,659,331 A | 4/1987 | Matthews et al. |
| 4,938,769 A | 7/1990 | Shaw |
| 4,944,757 A | 7/1990 | Martinez et al. |
| 5,019,103 A | 5/1991 | Van Zile et al. |
| 5,047,058 A | 9/1991 | Roberts et al. |
| 5,152,797 A | 10/1992 | Luckman et al. |
| 5,197,488 A | 3/1993 | Kovacevic |
| D338,270 S | 8/1993 | Stephens et al. |
| 5,282,866 A | 2/1994 | Cohen et al. |
| 5,306,276 A | 4/1994 | Johnson et al. |
| 5,344,458 A | 9/1994 | Bonutti |
| 5,356,414 A | 10/1994 | Cohen et al. |
| 5,364,401 A | 11/1994 | Ferrante et al. |
| 5,387,241 A | 2/1995 | Hayes |
| 5,464,406 A | 11/1995 | Ritter et al. |
| 5,470,354 A * | 11/1995 | Hershberger ......... A61F 2/4684 600/595 |
| 5,472,415 A | 12/1995 | King et al. |
| 5,486,178 A | 1/1996 | Hodge |
| 5,514,143 A | 5/1996 | Bonutti et al. |
| 5,540,696 A | 7/1996 | Booth, Jr. et al. |
| 5,569,260 A | 10/1996 | Petersen |
| 5,569,263 A | 10/1996 | Hein |
| 5,597,379 A | 1/1997 | Haines et al. |
| 5,601,565 A | 2/1997 | Huebner |
| 5,607,431 A | 3/1997 | Dudasik et al. |
| 5,611,802 A | 3/1997 | Samuelson et al. |
| 5,613,970 A | 3/1997 | Houston et al. |
| 5,643,272 A | 7/1997 | Haines et al. |
| 5,649,928 A | 7/1997 | Grundei |
| 5,683,469 A | 11/1997 | Johnson et al. |
| 5,690,636 A | 11/1997 | Wildgoose et al. |
| 5,702,464 A | 12/1997 | Lackey et al. |
| 5,704,941 A | 1/1998 | Jacober et al. |
| 5,709,689 A | 1/1998 | Ferrante et al. |
| 5,716,361 A | 2/1998 | Masini |
| 5,720,752 A | 2/1998 | Elliott et al. |
| 5,733,292 A | 3/1998 | Gustilo et al. |
| 5,735,904 A | 4/1998 | Pappas |
| 5,749,876 A | 5/1998 | Duvillier et al. |
| 5,766,261 A | 6/1998 | Neal et al. |
| 5,769,854 A | 6/1998 | Bastian et al. |
| 5,776,200 A | 7/1998 | Johnson et al. |
| 5,776,201 A | 7/1998 | Colleran et al. |
| 5,782,925 A | 7/1998 | Collazo et al. |
| 5,788,700 A | 8/1998 | Morawa et al. |
| 5,792,143 A | 8/1998 | Samuelson et al. |
| 5,860,969 A | 1/1999 | White et al. |
| 5,860,980 A | 1/1999 | Axelson, Jr. et al. |
| 5,860,982 A | 1/1999 | Ro et al. |
| 5,928,286 A | 7/1999 | Ashby et al. |
| 5,935,128 A | 8/1999 | Carter et al. |
| 5,941,884 A | 8/1999 | Corvelli et al. |
| 5,976,147 A | 11/1999 | Lasalle et al. |
| 5,989,261 A | 11/1999 | Walker et al. |
| 6,022,377 A | 2/2000 | Nuelle et al. |
| 6,024,746 A | 2/2000 | Katz |
| 6,080,196 A | 6/2000 | Bertin |
| 6,090,144 A | 7/2000 | Letot et al. |
| 6,102,953 A | 8/2000 | Huebner |
| 6,102,955 A | 8/2000 | Mendes et al. |
| 6,106,529 A | 8/2000 | Techiera |
| 6,159,216 A | 12/2000 | Burkinshaw et al. |
| 6,193,758 B1 | 2/2001 | Huebner |
| 6,214,052 B1 | 4/2001 | Burkinshaw |
| 6,277,123 B1 | 8/2001 | Maroney et al. |
| 6,344,043 B1 | 2/2002 | Pappas |
| 6,355,045 B1 | 3/2002 | Gundlapalli et al. |
| 6,478,799 B1 | 11/2002 | Williamson |
| 6,485,521 B1 | 11/2002 | Say et al. |
| 6,500,208 B1 * | 12/2002 | Metzger ......... A61F 2/389 623/20.15 |
| 6,641,614 B1 | 11/2003 | Wagner et al. |
| 6,660,039 B1 | 12/2003 | Evans et al. |
| 6,663,636 B1 | 12/2003 | Lin |
| 6,673,114 B2 | 1/2004 | Hartdegen et al. |
| 6,702,824 B2 | 3/2004 | Maroney et al. |
| 6,712,824 B2 | 3/2004 | Millard et al. |
| 6,723,097 B2 | 4/2004 | Fraser et al. |
| 6,736,852 B2 | 5/2004 | Callaway et al. |
| 6,743,258 B1 | 6/2004 | Keller |
| 6,746,487 B2 | 6/2004 | Scifert et al. |
| 6,821,470 B2 | 11/2004 | Gundlapalli et al. |
| 6,827,723 B2 | 12/2004 | Carson |
| 6,827,739 B2 | 12/2004 | Griner et al. |
| 6,916,324 B2 | 7/2005 | Sanford et al. |
| 6,916,340 B2 * | 7/2005 | Metzger ......... A61F 2/389 623/908 |
| 6,923,817 B2 | 8/2005 | Carson et al. |
| D518,178 S | 3/2006 | Christiansen |
| 7,104,996 B2 | 9/2006 | Bonutti |
| 7,105,026 B2 | 9/2006 | Johnson et al. |
| 7,135,044 B2 | 11/2006 | Bassik et al. |
| 7,141,067 B2 | 11/2006 | Jones et al. |
| 7,247,169 B2 | 7/2007 | Lo et al. |
| 7,291,174 B2 | 11/2007 | German et al. |
| 7,309,363 B2 | 12/2007 | Dietz |
| 7,338,496 B1 | 3/2008 | Winslow et al. |
| 7,338,499 B1 | 3/2008 | Kuczynski et al. |
| 7,344,541 B2 | 3/2008 | Haines et al. |
| 7,435,263 B2 | 10/2008 | Barnett et al. |
| 7,632,283 B2 | 12/2009 | Heldreth |
| 7,632,314 B2 | 12/2009 | Dietz |
| 7,634,306 B2 | 12/2009 | Sarin et al. |
| 7,658,767 B2 | 2/2010 | Wyss |
| 7,683,812 B2 | 3/2010 | Lewin |
| 7,691,150 B2 | 4/2010 | Cronin et al. |
| 7,695,519 B2 | 4/2010 | Collazo |
| 7,699,853 B2 | 4/2010 | Durand-Allen et al. |
| 7,731,755 B2 | 6/2010 | Wyss et al. |
| D619,251 S | 7/2010 | Justiniano-Garcia et al. |
| 7,837,690 B2 | 11/2010 | Metzger |
| 7,854,737 B2 | 12/2010 | Daniels et al. |
| 7,959,635 B1 | 6/2011 | Bonutti |
| 7,963,969 B2 | 6/2011 | Sanford |
| 8,012,215 B2 * | 9/2011 | Metzger ......... A61F 2/389 623/20.15 |
| 8,029,574 B2 | 10/2011 | Kellar et al. |
| 8,052,758 B1 | 11/2011 | Winslow |
| 8,065,927 B2 | 11/2011 | Crottet et al. |
| 8,066,777 B2 | 11/2011 | Palmer et al. |
| 8,070,752 B2 | 12/2011 | Metzger et al. |
| 8,070,823 B2 | 12/2011 | Kellar et al. |
| 8,092,545 B2 | 1/2012 | Coon et al. |
| 8,105,387 B2 | 1/2012 | Barnett et al. |
| 8,109,942 B2 | 2/2012 | Carson |
| 8,128,705 B2 | 3/2012 | Birkbeck et al. |
| 8,133,282 B2 | 3/2012 | Hushka et al. |
| 8,137,358 B2 | 3/2012 | Winslow et al. |
| 8,141,437 B2 | 3/2012 | Amirouche et al. |
| 8,142,512 B2 | 3/2012 | Brooks et al. |
| 8,187,283 B2 | 5/2012 | Thomas |
| 8,197,489 B2 | 6/2012 | Chessar et al. |
| 8,197,549 B2 | 6/2012 | Amirouche et al. |
| 8,231,631 B2 | 7/2012 | Lavallee et al. |
| D666,713 S | 9/2012 | Waite et al. |
| 8,357,166 B2 | 1/2013 | Aram et al. |
| 8,403,993 B2 | 3/2013 | Aram et al. |
| 8,414,653 B2 | 4/2013 | Burstein et al. |
| 8,419,740 B2 | 4/2013 | Aram et al. |
| 8,425,615 B2 | 4/2013 | Berelsman et al. |
| 8,435,304 B2 | 5/2013 | Dietz |
| 8,480,677 B2 | 7/2013 | Groh |
| 8,491,589 B2 | 7/2013 | Fisher et al. |
| 8,491,664 B2 | 7/2013 | McMahon et al. |
| 8,498,711 B2 | 7/2013 | Roche |
| 8,506,571 B2 | 8/2013 | Chana et al. |
| 8,529,578 B2 | 9/2013 | Daniels et al. |

(56) References Cited

U.S. PATENT DOCUMENTS

| | | | |
|---|---|---|---|
| 8,535,382 B2 | 9/2013 | Kehres et al. | |
| 8,551,179 B2 | 10/2013 | Jones et al. | |
| 8,568,485 B2 | 10/2013 | Ries et al. | |
| 8,585,710 B2 | 11/2013 | Fischer et al. | |
| 8,585,711 B2 | 11/2013 | Klotz et al. | |
| 8,591,593 B2 | 11/2013 | Metzger | |
| 8,597,358 B2 | 12/2013 | Landry et al. | |
| 8,603,101 B2 | 12/2013 | Claypool et al. | |
| 8,617,250 B2 | 12/2013 | Metzger | |
| 8,852,197 B2* | 10/2014 | Waite, II | A61B 17/1675 606/88 |
| 8,926,619 B2* | 1/2015 | Waite, II | A61B 17/1764 606/88 |
| 8,951,301 B2* | 2/2015 | Wogoman | A61F 2/4684 623/20.15 |
| 8,968,412 B2* | 3/2015 | Wogoman | A61F 2/4684 623/20.29 |
| 8,979,847 B2 | 3/2015 | Belcher et al. | |
| 8,986,390 B2* | 3/2015 | Wogoman | A61F 2/4684 623/20.29 |
| 9,114,012 B2* | 8/2015 | Wogoman | A61F 2/4684 |
| 9,132,011 B2* | 9/2015 | Wogoman | A61F 2/28 |
| 9,314,257 B2* | 4/2016 | Waite, II | A61F 2/389 |
| 9,402,747 B2* | 8/2016 | Wogoman | A61F 2/4684 |
| 9,861,491 B2* | 1/2018 | Waite, II | A61B 17/1764 |
| 10,265,183 B2* | 4/2019 | Waite, II | A61F 2/389 |
| 10,952,863 B2* | 3/2021 | Waite, II | A61F 2/4684 |
| 2001/0053935 A1 | 12/2001 | Hartdegen et al. | |
| 2002/0082607 A1* | 6/2002 | Heldreth | A61F 2/4684 606/102 |
| 2003/0093156 A1* | 5/2003 | Metzger | A61F 2/389 623/20.15 |
| 2004/0039450 A1 | 2/2004 | Griner et al. | |
| 2004/0097951 A1 | 5/2004 | Steffensmeier | |
| 2004/0186583 A1 | 9/2004 | Keller | |
| 2004/0225368 A1 | 11/2004 | Plumet et al. | |
| 2005/0075640 A1 | 4/2005 | Collazo et al. | |
| 2005/0246027 A1* | 11/2005 | Metzger | A61F 2/4637 623/20.15 |
| 2006/0069447 A1 | 3/2006 | DiSilvestro et al. | |
| 2006/0089641 A1 | 4/2006 | Collazo | |
| 2006/0111790 A1 | 5/2006 | Dietz | |
| 2006/0184176 A1 | 8/2006 | Straszheim-Morley et al. | |
| 2007/0233137 A1 | 10/2007 | Seo et al. | |
| 2007/0239165 A1 | 10/2007 | Amirouche | |
| 2008/0004708 A1 | 1/2008 | Wyss | |
| 2008/0091273 A1 | 4/2008 | Hazebrouck | |
| 2008/0114464 A1 | 5/2008 | Barnett et al. | |
| 2008/0119938 A1 | 5/2008 | Oh | |
| 2008/0147075 A1 | 6/2008 | Bonutti | |
| 2008/0154270 A1 | 6/2008 | Haines et al. | |
| 2008/0221569 A1 | 9/2008 | Moore et al. | |
| 2008/0269901 A1 | 10/2008 | Baynham et al. | |
| 2009/0076514 A1 | 3/2009 | Haines | |
| 2009/0082773 A1 | 3/2009 | Haines | |
| 2009/0084491 A1 | 4/2009 | Uthgenannt et al. | |
| 2009/0125114 A1 | 5/2009 | May et al. | |
| 2009/0138018 A1 | 5/2009 | Haines | |
| 2009/0216325 A1 | 8/2009 | May et al. | |
| 2009/0240254 A1 | 9/2009 | Arnhold | |
| 2009/0265013 A1 | 10/2009 | Mandell | |
| 2010/0010635 A1 | 1/2010 | Straszheim-Morley et al. | |
| 2010/0016979 A1 | 1/2010 | Wyss et al. | |
| 2010/0063594 A1 | 3/2010 | Hazebrouck et al. | |
| 2010/0076438 A1 | 3/2010 | Correia et al. | |
| 2010/0082111 A1 | 4/2010 | Thomas | |
| 2010/0125337 A1 | 5/2010 | Greece et al. | |
| 2010/0298941 A1 | 11/2010 | Hes et al. | |
| 2010/0305711 A1 | 12/2010 | McKinnon et al. | |
| 2011/0066246 A1 | 3/2011 | Ries et al. | |
| 2011/0178605 A1 | 7/2011 | Auger et al. | |
| 2012/0041566 A1 | 2/2012 | Lenz et al. | |
| 2012/0158152 A1* | 6/2012 | Claypool | A61F 2/461 623/20.32 |
| 2012/0209391 A1 | 8/2012 | Cipolletti et al. | |
| 2012/0226481 A1 | 9/2012 | Carson | |
| 2012/0239160 A1 | 9/2012 | Belew et al. | |
| 2012/0259339 A1 | 10/2012 | Hood et al. | |
| 2012/0259421 A1 | 10/2012 | Satterthwaite et al. | |
| 2012/0265317 A1 | 10/2012 | Metzger | |
| 2012/0310246 A1 | 12/2012 | Belcher et al. | |
| 2012/0323334 A1 | 12/2012 | Jones et al. | |
| 2013/0006252 A1* | 1/2013 | Waite, II | A61F 2/4684 606/88 |
| 2013/0006253 A1* | 1/2013 | Waite, II | A61B 17/1675 606/88 |
| 2013/0006370 A1* | 1/2013 | Wogoman | A61F 2/4684 623/20.16 |
| 2013/0006371 A1* | 1/2013 | Wogoman | A61F 2/461 623/20.21 |
| 2013/0006376 A1* | 1/2013 | Wogoman | A61F 2/389 606/88 |
| 2013/0006377 A1* | 1/2013 | Waite, II | A61F 2/30749 623/20.32 |
| 2013/0006378 A1* | 1/2013 | Wogoman | A61F 2/3859 623/20.35 |
| 2013/0013075 A1 | 1/2013 | Fisher et al. | |
| 2013/0020733 A1 | 1/2013 | Berger | |
| 2013/0024001 A1 | 1/2013 | Wentorf et al. | |
| 2013/0030538 A1 | 1/2013 | Metzger et al. | |
| 2013/0046385 A1 | 2/2013 | Hartdegen et al. | |
| 2013/0079671 A1 | 3/2013 | Stein et al. | |
| 2013/0096567 A1 | 4/2013 | Fisher et al. | |
| 2013/0103153 A1 | 4/2013 | Blackwell et al. | |
| 2013/0103160 A1 | 4/2013 | Young | |
| 2013/0173011 A1 | 7/2013 | Otto et al. | |
| 2013/0184834 A1 | 7/2013 | Brooks et al. | |
| 2013/0190885 A1 | 7/2013 | Ammann et al. | |
| 2013/0204267 A1 | 8/2013 | Dietz | |
| 2013/0204377 A1 | 8/2013 | Samuelson et al. | |
| 2013/0211531 A1 | 8/2013 | Steines et al. | |
| 2013/0245769 A1 | 9/2013 | Gimbel et al. | |
| 2013/0245803 A1 | 9/2013 | Lang | |
| 2013/0261505 A1 | 10/2013 | Sherman et al. | |
| 2013/0261758 A1 | 10/2013 | Claypool et al. | |
| 2013/0261759 A1* | 10/2013 | Claypool | A61B 5/1036 623/20.33 |
| 2013/0282132 A1 | 10/2013 | White et al. | |
| 2013/0289569 A1 | 10/2013 | Wilkinson | |
| 2013/0289726 A1 | 10/2013 | Curran et al. | |
| 2013/0304221 A1 | 11/2013 | Blaylock et al. | |
| 2014/0039636 A1 | 2/2014 | Kuntz | |
| 2014/0052269 A1 | 2/2014 | Claypool et al. | |
| 2014/0066934 A1 | 3/2014 | Deirmengian et al. | |
| 2014/0081412 A1 | 3/2014 | Metzger | |
| 2014/0155902 A1 | 6/2014 | Sikora et al. | |
| 2014/0156017 A1 | 6/2014 | Salyer | |
| 2014/0159282 A1 | 6/2014 | Smith et al. | |
| 2014/0172112 A1 | 6/2014 | Marten | |
| 2014/0276858 A1 | 9/2014 | Major et al. | |
| 2014/0277539 A1 | 9/2014 | Cook et al. | |
| 2015/0313727 A1* | 11/2015 | Waite, II | A61F 2/389 623/20.32 |
| 2018/0125666 A1* | 5/2018 | Waite, II | A61F 2/389 |
| 2019/0240033 A1* | 8/2019 | Waite, II | A61F 2/389 |
| 2021/0205089 A1* | 7/2021 | Waite, II | A61F 2/4684 |

FOREIGN PATENT DOCUMENTS

| | | |
|---|---|---|
| CN | 103379880 A | 10/2013 |
| EP | 0890340 A2 | 1/1999 |
| EP | 1219269 A1 | 7/2002 |
| EP | 1415625 A2 | 5/2004 |
| EP | 1836997 A1 | 9/2007 |
| EP | 2168537 A1 | 3/2010 |
| EP | 2540256 A1 | 1/2013 |
| GB | 2323037 A | 9/1998 |
| WO | 9925263 A1 | 5/1999 |
| WO | 0013597 A1 | 3/2000 |
| WO | 2008024836 A2 | 2/2008 |

(56) References Cited

FOREIGN PATENT DOCUMENTS

| WO | 2008054389 A1 | 5/2008 |
|---|---|---|
| WO | 2011073632 A1 | 6/2011 |
| WO | 2013006823 A1 | 1/2013 |

OTHER PUBLICATIONS

Zimmer NexGen LCCK, Surgical Technique for use with LCCK 4-in-1 Instrument, 2009, 52 pages.
DePuy Orthopaedics, Inc., Sigma Revision and M.B.T. Revision Tray, Surgical Technique, 2008, 82 pages.
Smith & Nephew, Legion, Revision Knee System, Surgical Technique, 2005, 40 pages.
Biomet, Vanguard SSK, Revision System, Surgical Technique, Feb. 2008, 64 pages.
GMK Revision, Surgical Technique, Ref. 99.27.12US rev. 1, 1999, 74 pages.
PFC Sigma RP-F, Specialist 2 Instruments, Surgical Technique, Performance in Flexion, 2007, 32 pages.
P.F.C. Sigma Rotating Platform Knee System with M.B.T Tray, Primary Procedure with a Curved or Posterior Stabilized Implant, 2003, 43 pages.
LCS High Performance Instruments, Surgical Technique, 2008, 44 pages.
Sigma High Performance Instruments, Design Rationale, 2007, 12 pages.
Sigma High Performance Instruments, Classic Surgical Technique, 2010, 52 pages.
Coordinate Ultra Revision Knee System, Surgical Technique, 1997, p. 24.
P.F.C. Sigma Knee System, Revision, Surgical Technique, 2000, p. 66.
Sigma Revision and M.B.T. Revision Tray, Surgical Technique, 2012, p. 84.
S-Rom Noiles Rotating Hinge, Surgical Technique, 2012, p. 76.
European Search Report for European Application No. 12174178. 9-2310, Sep. 6, 2012, 6 pages.
Declaration of Thomas E. Wogoman (with Exhibits A-I), executed Aug. 11, 2014, 145 pages.
Extended European Search Report, European Application No. 16194469. 9-1664 / 3158953, dated Jun. 22, 2017, 13 pages.
Australian Examination Report for Appln No. 2021201926, dated Apr. 5, 2022, 2 pages.

\* cited by examiner

TIBIAL TRIAL SYSTEM FOR A KNEE PROSTHESIS AND METHOD

This application is a continuation application and claims priority to U.S. patent application Ser. No. 16/390,667, now U.S. Pat. No. 10,952,863, which is a continuation application that claims priority under 35 U.S.C. § 121 to U.S. patent application Ser. No. 15/866,047, now U.S. Pat. No. 10,265,183, which is a divisional application that claims priority under 35 U.S.C. § 121 to U.S. patent application Ser. No. 14/265,960, now U.S. Pat. No. 9,861,491, each of which is expressly incorporated herein by reference.

CROSS-REFERENCE

Cross-reference is made to U.S. patent application Ser. No. 13/530,771, now U.S. Pat. No. 8,986,390, entitled "SYSTEM AND METHOD FOR TRIALING A KNEE PROSTHESIS" by Tom Wogoman et al. and filed on Jun. 22, 2012, U.S. patent application Ser. No. 13/530,662, now U.S. Pat. No. 8,951,301, entitled "METHOD OF USING A TRIALING SYSTEM FOR A KNEE PROSTHESIS" by Tom Wogoman et al. and filed on Jun. 22, 2012, and U.S. patent application Ser. No. 13/530,649, now U.S. Pat. No. 8,968,412, entitled "TRIALING SYSTEM FOR A KNEE PROSTHESIS AND METHOD OF USE" by Tom Wogoman et al. and filed on Jun. 22, 2012, each of which is assigned to the same assignee as the present application, and each of which is hereby incorporated by reference.

TECHNICAL FIELD

The present disclosure relates generally to orthopaedic surgical instruments and, more particularly, to surgical instruments used with a patient's tibia.

BACKGROUND

Joint arthroplasty is a well-known surgical procedure by which a diseased and/or damaged natural joint is replaced by a prosthetic joint. A typical knee prosthesis includes a patella prosthetic component, a tibial tray, a femoral component, and a polymer insert or bearing positioned between the tibial tray and the femoral component. Femoral components are designed to be attached to a surgically-prepared distal end of a patient's femur. Tibial trays are designed to be attached to a surgically-prepared proximal end of a patient's tibia.

To facilitate the replacement of the natural joint with the knee prosthesis, orthopaedic surgeons use a variety of orthopaedic surgical instruments such as, for example, prosthetic trial components, cutting blocks, drill guides, milling guides, and other surgical instruments. Prosthetic trial components, such as, for example, a femoral trial component and a tibial bearing trial component, are used to size and select the components of the knee prosthesis that will replace the patient's natural joint. A procedure that utilizes the trial components to size and select the components of the knee prosthesis is often referred to as a trial reduction.

SUMMARY

According to one aspect of the disclosure, an orthopaedic surgical instrument system for use during a surgical procedure to implant an orthopaedic knee prosthesis includes a tibial base trial component adapted to be positioned on a surgically-prepared proximal end of a patient's tibia. The tibial base trial component has an opening defined therein. The instrument system also includes an insert component shaped to be received in the opening defined in the tibial base trial component. The insert component has a base plate and a central post extending upwardly from a superior surface of the base plate. A superior surface of the central post has a ramp surface defined therein, with the ramp surface inclining superiorly in the anterior-to-posterior direction. The instrument system also includes a tibial bearing trial component having an opening defined therein. The central post of the insert component is configured to be received in the opening of the tibial bearing trial assembly.

The central post may include a collar extending outwardly from the longitudinal axis of the central post, with the ramp surface being defined in a superior surface of the collar. Such a ramp surface defined in the collar may include an anterior end and a posterior end. The anterior end of the ramp surface defined in the collar is coplanar with the superior surface of the base plate, and the posterior end of the ramp surface defined in the collar is spaced apart superiorly from the superior surface of the base plate.

The central post may include a connector configured to secure the insert component to a surgical handle. The connector includes a flange extending anteriorly away from the longitudinal axis of the central post, with the ramp surface being defined in a superior surface of the flange of the connector.

The central post may also include an elongated anti-rotation lug extending in a direction away from the longitudinal axis of the central post, with the ramp surface being defined in a superior surface of the elongated anti-rotation lug.

The insert component may be embodied as a tibial evaluation component having a pair of bone engaging spikes extending inferiorly from the inferior surface thereof.

The tibial bearing trial component may include a tibial bearing surface trial component having an articular surface, and a shim removably secured to the tibial bearing surface trial component.

The insert component may be embodied as a keel punch, with the keel punch having a pair of serrated wings extending inferiorly from the inferior surface of the insert component.

According to another aspect, a surgical instrument for use to surgically prepare a proximal end of a patient's tibia during a surgical procedure to implant an orthopaedic knee prosthesis includes a keel punch. The keel punch includes a base plate, and a central post extending upwardly from a superior surface of the base plate. A superior surface of the central post has a ramp surface defined therein, with the ramp surface inclining superiorly in the anterior-to-posterior direction. The keel punch also includes pair of serrated wings extending inferiorly from an inferior surface of the base plate.

The central post may include a collar extending outwardly from the longitudinal axis of the central post, with the ramp surface being defined in a superior surface of the collar. The anterior end of the ramp surface defined in the collar is coplanar with the superior surface of the base plate, and the posterior end of the ramp surface defined in the collar is spaced apart superiorly from the superior surface of the base plate.

The central post may include a connector configured to secure the keel punch to a surgical handle. The connector includes a flange extending anteriorly away from the longitudinal axis of the central post, and the ramp surface is defined in a superior surface of the flange of the connector.

The central post may further include an elongated anti-rotation lug extending in a direction away from the longitudinal axis of the central post. The ramp surface is defined in a superior surface of the elongated anti-rotation lug.

The surgical punch further may further include a tapered cylindrical post extending inferiorly from the inferior surface of the base plate. One of the pair of serrated wings is secured to a medial side of the tapered cylindrical post and extends medially therefrom, with the other serrated wing being secured to a lateral side of the tapered cylindrical post and extending laterally therefrom.

According to another aspect, a method of trialing prosthetic components of a knee prosthesis includes positioning a tibial base trial component on a surgically-prepared proximal end of a patient's tibia, and inserting an insert component into an opening defined in the tibial base trial component. The insert component has a base plate and a central post extending upwardly from a superior surface of the base plate. The superior surface of the central post has a ramp surface defined therein. The method also includes advancing a tibial bearing trial component in the anterior-to-posterior direction such that a leading edge of the tibial bearing trial component contacts, and rides up, the ramp surface so as to urge a posterior edge of the tibial bearing trial component superiorly in a direction away from the tibial base trial component.

A femoral trial component and the tibial base trial component are urged in a direction away from one another during advancement of the tibial bearing trial component.

The tibial bearing trial component may a tibial bearing surface trial component secured to a shim. A leading edge of the shim contacts, and rides up, the ramp surface so as to urge a posterior edge of the tibial bearing surface trial component superiorly in a direction away from the tibial base trial component during advancement of the tibial bearing trial component.

The central post comprises a collar extending outwardly from the longitudinal axis of the central post, with the ramp surface being defined in a superior surface of the collar. A leading edge of the shim contacts, and rides up, the ramp surface of the collar so as to urge a posterior edge of the tibial bearing surface trial component superiorly in a direction away from the tibial base trial component during advancement of the tibial bearing trial component.

The central post includes a connector configured to secure the insert component to a surgical handle. The connector includes a flange extending anteriorly away from the longitudinal axis of the central post, with the ramp surface being defined in a superior surface of the flange of the connector. A leading edge of the tibial bearing surface trial component contacts, and rides up, the ramp surface of the connector so as to urge a posterior edge of the tibial bearing surface trial component superiorly in a direction away from the tibial base trial component during advancement of the tibial bearing trial component.

The central post also includes an elongated anti-rotation lug extending in a direction away from the longitudinal axis of the central post, with the ramp surface being defined in a superior surface of the elongated anti-rotation lug. A leading edge of the shim contacts, and rides up, the ramp surface of the anti-rotation lug so as to urge a posterior edge of the tibial bearing surface trial component superiorly in a direction away from the tibial base trial component during advancement of the tibial bearing trial component.

The insert component may define a tibial evaluation component, with the tibial evaluation component having a pair of bone engaging spikes extending inferiorly from the inferior surface of the insert component. The bone engaging spikes of the tibial evaluation component are inserted through the opening defined in the tibial base trail component and into bone tissue.

The insert component may be embodied as a keel punch, with the keel punch having a pair of serrated wings extending inferiorly from the inferior surface of the insert component. The serrated wings of the keel punch are inserted through the opening defined in the tibial base trail component and into bone tissue.

BRIEF DESCRIPTION OF THE DRAWINGS

The detailed description particularly refers to the following figures, in which.

DETAILED DESCRIPTION OF THE DRAWINGS

Figure 1:
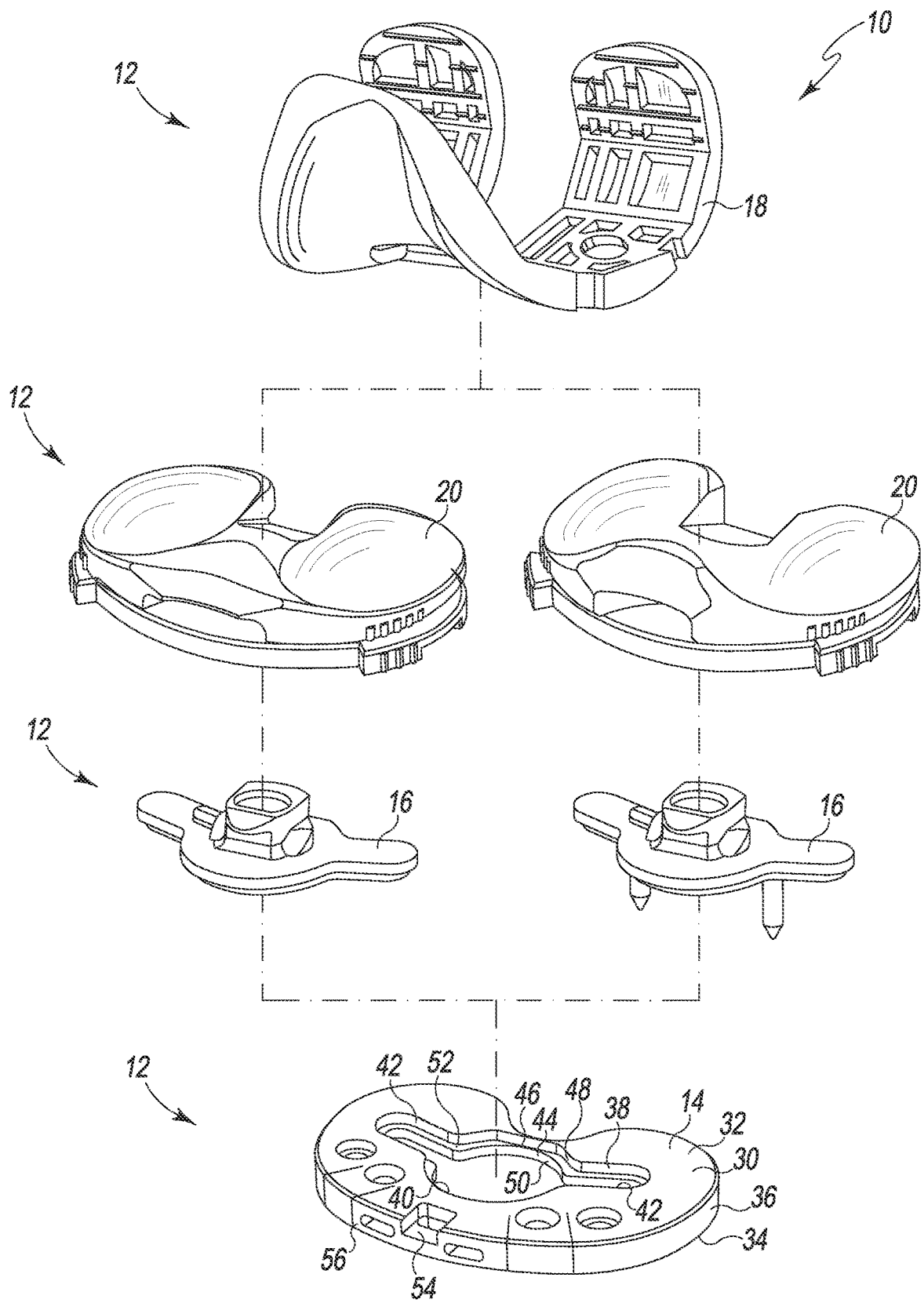
FIG. 1 is an exploded perspective view of an orthopaedic surgical instrument system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopedics. Use of such anatomical reference terms in the written description and claims is intended to be consistent with their well-understood meanings unless noted otherwise.

Referring to FIGS. 1-11, an orthopaedic surgical instrument system 10 (hereinafter system 10) is shown. The system 10 is used during joint arthroplasty procedures, such as a total knee replacement procedure. It should be appreciated, however, that although the system 10 is described below in regard to the performance of a total knee replacement procedure, certain concepts associated with the system 10 may be utilized in replacement procedures of numerous other joints throughout the body.

As shown in FIG. 1, the system 10 has a number of trial components 12, including a tibial base trial component 14, a number of insert components 16, a femoral trial component 18, and a number of tibial bearing trial components 20. The system 10 also includes a tibial keel punch 22 (see FIG. 7) and a number of surgical tools, such as, for example, an alignment handle 26 and an impaction handle 28 (see FIG. 12), which are used to manipulate the trial components 12 and the other surgical instruments during the performance of an orthopaedic surgical procedure, as described in greater detail below.

The system 10 may be utilized to size and select the prosthetic components of a knee prosthesis that will replace the patient's natural joint. To do so, the femoral trial component 18 is attached to a surgically-prepared distal end 600 of a patient's femur 602 (see FIG. 13), whereas the tibial base trial component 14 is attached to a surgically-prepared proximal end 604 of a patient's tibia 606 (see FIG. 13). One of the tibial bearing trial components 20 is positioned on the tibial base trial component 14 between the femoral trial component 18 and the tibial base trial component 14. As described in greater detail below, the surgeon uses the system 10 in a trial reduction process to determine the type and configuration of each of the various types of prosthetic components that are to be implanted.

The system 10 may be also utilized to surgically prepare the proximal end 604 of a patient's tibia 606 for implantation of a tibial prosthetic component, such as a tibial tray, during the performance of an orthopaedic surgical procedure. The tibial base trial component 14 and the guide tower 24 are positioned on the proximal end 604 of the patient's tibia 606, and the surgeon uses the trial component 14 and the tower 24 to guide, for example, a surgical drill while reaming the proximal end 604 of the patient's tibia 606. Thereafter, the keel punch 22 is impacted into the proximal end 604 of the patient's tibia 606 before the guide tower 24 is removed. An additional trial reduction may be performed with the keel punch 22 before the surgeon installs the components of the knee prosthesis, as described in greater detail below.

As can be seen in FIG. 1, the base trial component 14 includes a plate 30 having an upper surface 32, a lower surface 34, and an outer sidewall 36 extending between the surfaces 32, 34. The plate 30 has a plate opening 38 defined in the upper surface 32. The plate opening 38 has a central opening 40 and a pair of elongated openings 42 extending outwardly therefrom. An inner wall 44 extends downwardly from the opening 38 to define a passageway 46 through the plate 30. The inner wall 44 includes an upper wall 48 and a lower wall 50 offset or otherwise spaced inwardly from the upper wall 48. The upper wall 48 and lower wall 50 cooperate to define a shelf surface 52 therebetween. As will be discussed in greater detail below, the configuration of the passageway 46 permits the advancement of various surgical drills, punches, and other instruments into the proximal end 604 of the patient's tibia 606. It should be appreciated that the tibial base trial component 14 may be formed in a number of different sizes to accommodate tibias of various sizes.

The plate 30 also includes a lever-receiving notch 54 that is defined in an anterior aspect 56 thereof. The notch 54 is configured to receive a lever 66 associated with the alignment handle 26 (see FIG. 15).

Referring now to FIGS. 2-5, the insert component 16 is embodied as a tibial evaluation component or "evaluation bullet". The tibial evaluation components 16 are configured to be positioned separately in the plate opening 38 of the base trial component 14. Each tibial evaluation component 16 has a base plate 78 having a peripheral rim 82 defined therein. The rim 82 has an inferior surface 84 configured to engage the shelf surface 52 of the base trial component 14 when the tibial evaluation component 16 is seated on the base trial component 14. The base plate 78 includes a central platform 86 sized to be received in the central opening 40 of the base trial component 14. The body 80 also includes a pair of prongs 88, 90 that extend outwardly from the central platform 86. The prongs 88, 90 are sized to be received in the elongated openings 42 of the base trial component 14.

The base plate 78 of the tibial evaluation component 16 includes a central post 94 extending upwardly from a superior surface 96 thereof. The post 94 has a connector 98 formed in its superior end. The connector 98 is configured to receive a locking flange associated with the impaction handle 28 so as to secure the tibial evaluation component 16 to the handle 28. The connector 98 includes a flange 100 that extends anteriorly away from the longitudinal axis of the central post 94. The flange 100 has a ramp surface 102 defined therein. In particular, an inferior surface 104 of the flange 100 extends substantially parallel to the superior surface 96 of the tibial evaluation component's base plate 78, whereas the flange's superior surface 106 inclines superiorly in the anterior-to-posterior direction. In other words, as can be seen clearly in FIG. 3, the anterior edges of the flange's superior surface 106 and inferior surface 104 converge on one another to form a leading edge 108 of the flange 100. The superior surface 106 inclines superiorly in the anterior-to-posterior direction such that the distance in which the superior surface 106 of the flange 100 is spaced apart from the inferior surface 104 is greater at the end of the flange 100 opposite its leading edge 108. As will be discussed below in greater detail, such a ramp surface facilitates installation of the tibial bearing trial assembly 20.

Figure 2:
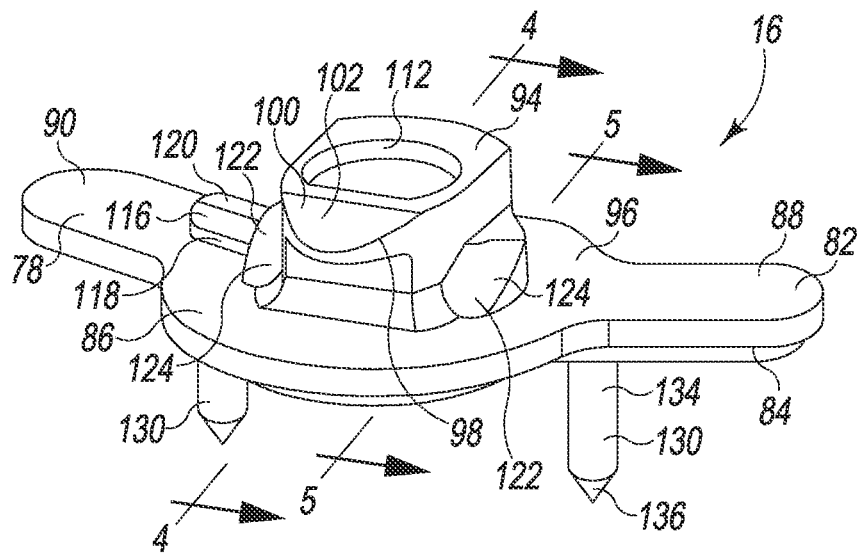
FIG. 2 is a perspective view of the tibial evaluation component of the orthopaedic surgical instrument system of FIG. 1.
Figure 3:
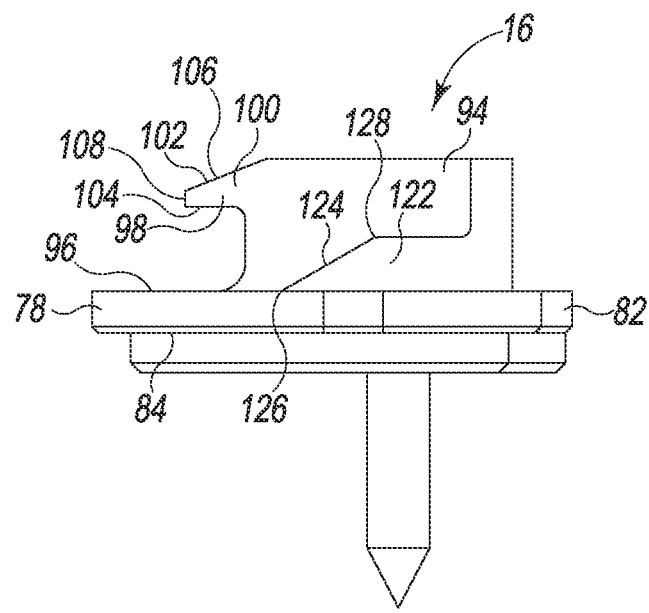
FIG. 3 is a side elevation view of the tibial evaluation component of FIG. 2.
Figure 4:
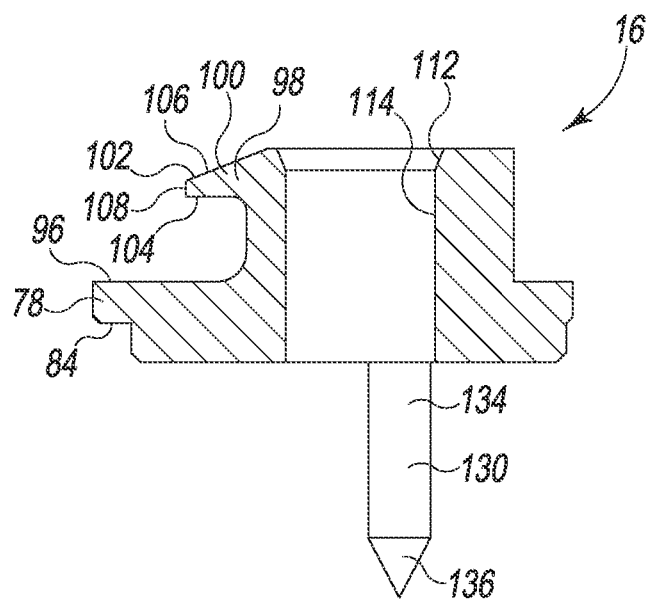
FIG. 4 is a cross sectional view of the tibial evaluation component taken along the line 4-4 of FIG. 2, as viewed in the direction of the arrows.
Figure 5:
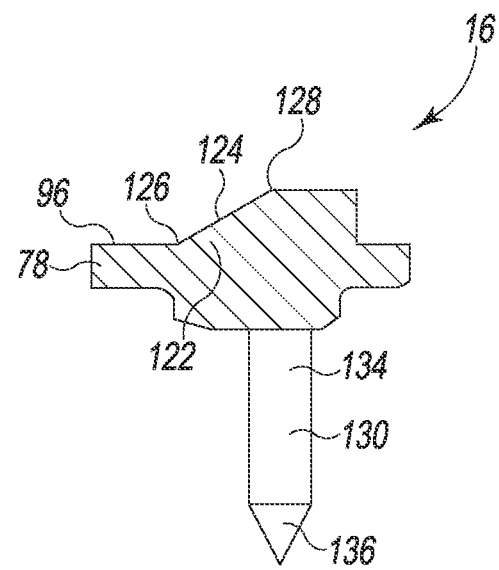
FIG. 5 is a cross sectional view of the tibial evaluation component taken along the line 5-5 of FIG. 2, as viewed in the direction of the arrows.

As shown best in FIGS. 2 and 4, the central post 94 also has an opening 112 defined in its superior end. An inner wall extends downwardly from the opening 112 to define a central passageway 114 through the tibial evaluation component 16. The opening 112 is configured to receive a guide pin (not shown) associated with the impaction handle 28 (see FIG. 12). The inner wall of the central passageway 114 has a keyed section (not shown) that permits the tibial evaluation component 16 to be attached to the impaction handle 28 in only a single predetermined orientation.

The central post 94 of the tibial evaluation component 16 has an anti-rotation block or lug 120 extending outwardly from the post's curved sidewall toward the prong 90. As will be described in greater detail below, the anti-rotation lug 120 engages the tibial bearing trial component 20 to prevent or permit the tibial bearing trial component 20 from rotating relative to the tibial base trial component 14. It should be appreciated that in other embodiments the lug 120 might be formed in, for example, the other side of the central post 94 so as to extend toward the prong 88. It should also be appreciated that in other embodiments the tibial evaluation component 16 may include additional anti-rotation lugs. In the illustrative embodiment, the anti-rotation lug 120 has a ramp surface 116 defined therein. In particular, as can be seen in FIG. 2, a portion of the lug's anterior superior surface 118 inclines superiorly in the anterior-to-posterior direction. As will be discussed below in greater detail, such a ramp surface 116 facilitates installation of the tibial bearing trial assembly 20.

The central post 94 of the tibial evaluation component 16 has a pair of collars 122 extending outwardly from the longitudinal axis of the post 94. As can be seen in FIG. 2, one of the collars 122 extends outwardly toward the prong 90, with the other collar extending toward the prong 88. The superior surface of each of the collars 122 has a ramp surface 124 defined therein. The collar's ramp surface 124 inclines superiorly in the anterior-to-posterior direction. In particular, as can be seen best in FIGS. 3 and 5, an anterior end 126 of the ramp surface 124 is coplanar with the superior surface 96 of the tibial evaluation component's base plate 78, whereas the ramp surface's posterior end 128 is spaced apart superiorly from the superior surface 96 of the tibial evaluation component's base plate 78. As a result, the ramp surface 124 inclines superiorly in the anterior-to-posterior direction. As will be discussed below in greater detail, such a ramp surface facilitates installation of the tibial bearing trial assembly 20.

Returning to FIG. 1, the tibial evaluation component 16 may be embodied as a spiked component and a spikeless component. The spiked tibial evaluation component 16 includes a pair of mounting spikes 130 that extend downwardly from the prongs 88, 90, respectively. Each spike 130 includes an upper cylindrical section 134 and a pointed conical tip 136 configured to engage the proximal end 604 of the patient's tibia 606, thereby temporarily securing the base insert 126 to the proximal end 604 of the patient's tibia 606.

Figure 13:
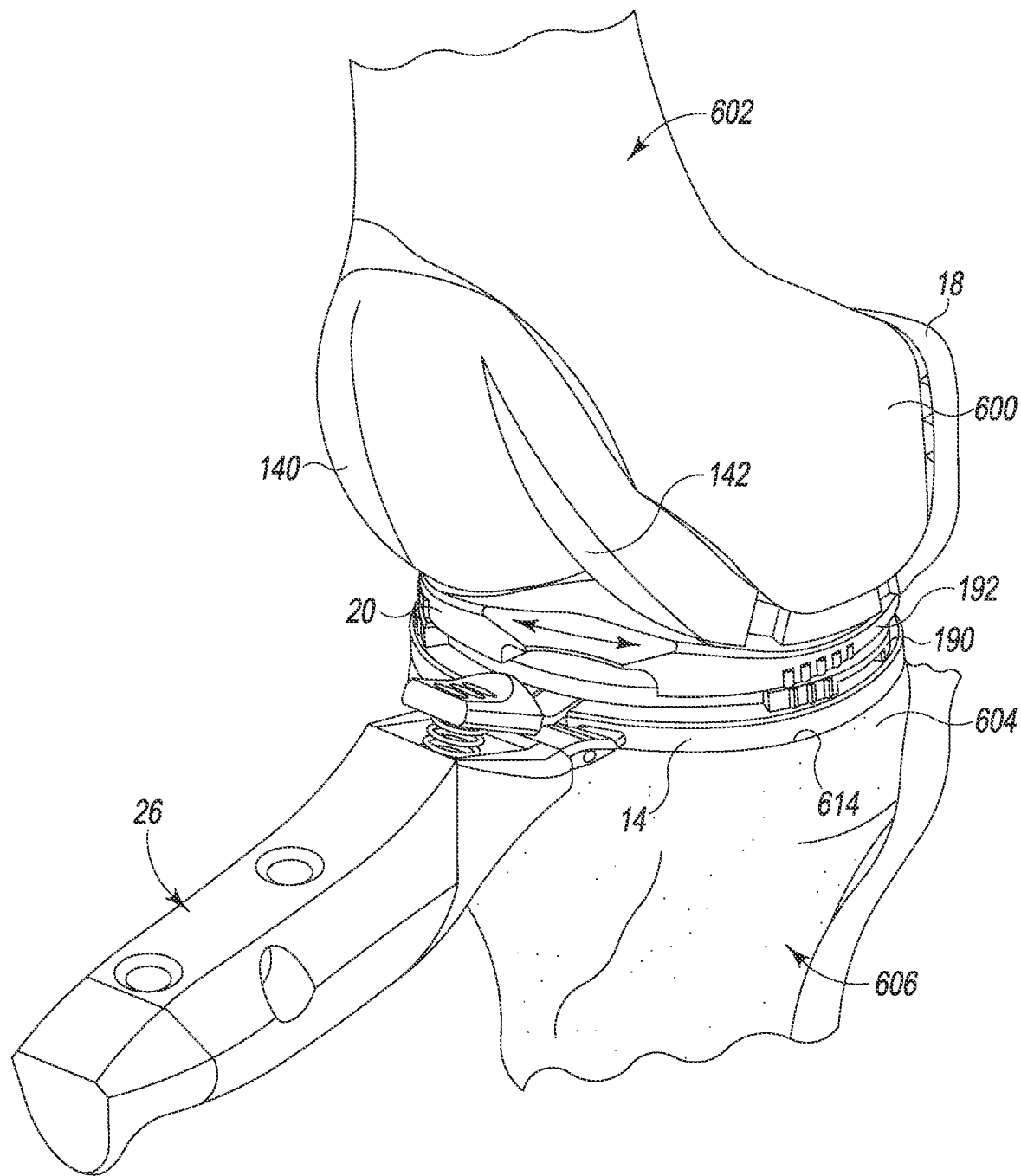

As discussed above, the system 10 also includes a femoral trial component 18 that is configured to be secured to the distal end 600 of the patient's femur 602 (see FIG. 13). One example of a femoral trial is shown and described in co-pending U.S. patent application Ser. No. 13/530,239, which published as U.S. Patent App. Pub. No. 2013/0006378 and is entitled "POLYMER FEMORAL TRIAL COMPONENT" by Thomas Wogoman and filed Jun. 22, 2012, which is expressly incorporated herein by reference. The femoral trial component 18 is configured to assist the surgeon in selecting a femoral prosthetic component, which will emulate the configuration of the patient's natural femoral condyles. As such, the femoral trial component 18 includes a pair of condyle surfaces 140, 142, which may be shaped (i.e., curved) in a manner that approximates the condyles of the natural femur.

Figure 6:
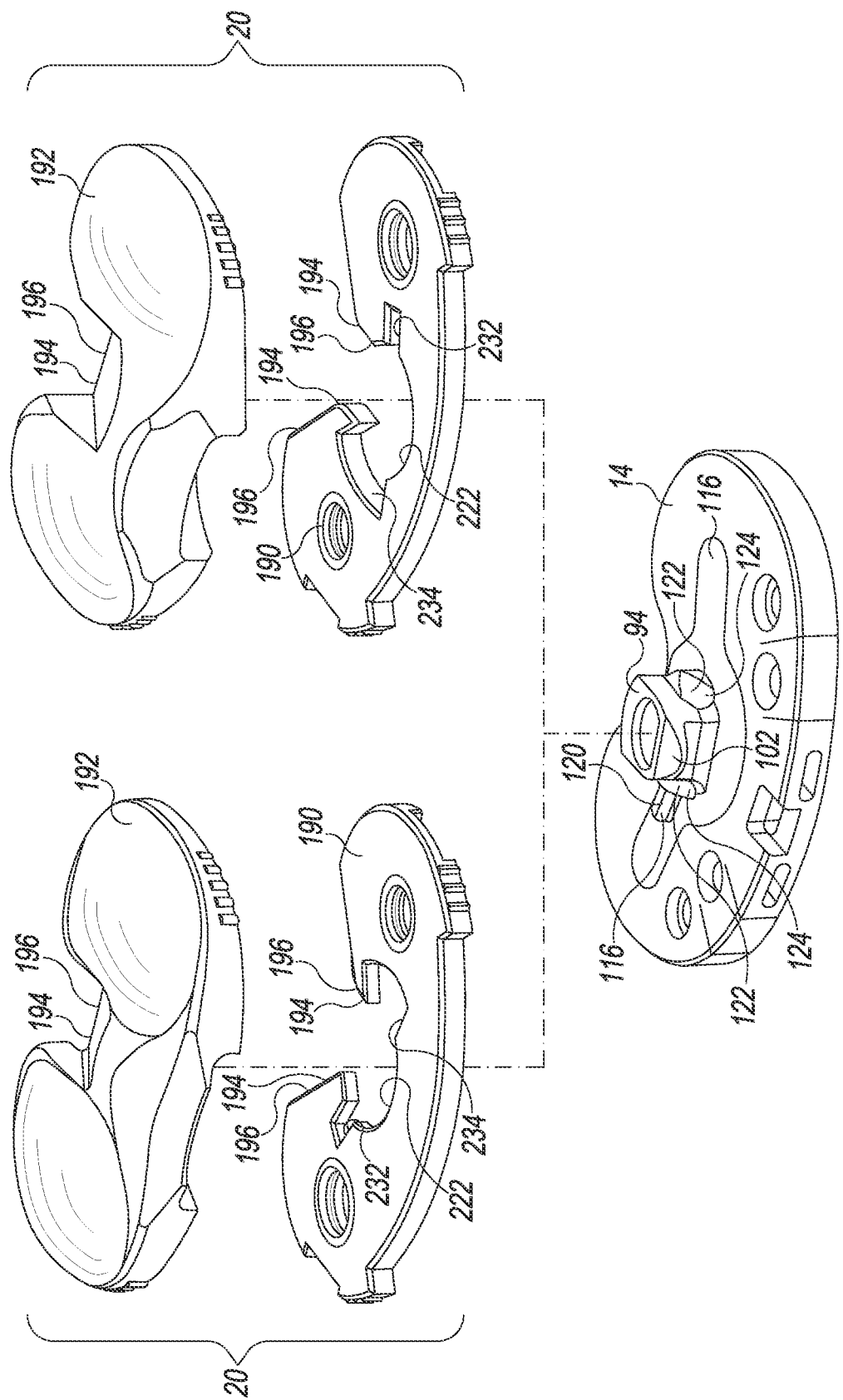
FIG. 6 is an exploded perspective view of the tibial base trial component, the tibial evaluation component, and a number of tibial bearing trial components of the orthopaedic surgical instrument system of FIG. 1.

Referring now to FIG. 6, a number of tibial bearing trial components 20 of the system 10 are shown. As discussed above, in the illustrative embodiment described herein, the tibial bearing trial components 20 are a multi-piece assembly configured to assist the surgeon in selecting a size and configuration of a prosthetic tibial bearing component of the knee prosthesis. As shown in FIG. 6, a given tibial bearing trial component 20 may be assembled with one of a number of tibial bearing surface trial components 192 and one of a number of a plurality of trial shims 190. In an embodiment, the bearing surface trial components 192 may be provided in different sizes and/or configurations, and each shim 190 may have a different thickness. Because each shim 190 is configured to be secured to each bearing surface trial component 192, the surgeon is able to assemble a tibial bearing trial component 20 of one size and configuration, evaluate the performance of that tibial bearing trial component 20, and then modify the tibial bearing trial component 20 as necessary to determine intraoperatively the type and configuration of the prosthetic tibial bearing component to be implanted.

As can be seen in FIG. 6, each of the tibial bearing trial components 20 has a leading edge 194 defined in a posterior surface 196 thereof. As will be described in greater detail below, during installation of the tibial bearing trial component 20, the leading edge 194 of the tibial bearing trial component 20 contacts and rides up the ramp surfaces of the tibial evaluation component 16 so as to facilitate installation of the tibial bearing trial component 20 without subluxation of the patient's tibia 606.

Returning to FIG. 6, one of the bearing surface trial components 192 is a fixed bearing surface trial component. The term "fixed bearing surface trial component" as used herein refers to a bearing surface trial that is fixed in position relative to the tibial base trial component 14 when the bearing surface trial component 192 and shim 190 are attached thereto (i.e., it is configured to not substantially rotate or move in the anterior-posterior direction or medial-lateral direction relative to the tibial base trial component 14). Such a fixed bearing surface trial component 192 may be embodied as a cruciate retaining trial, a posterior stabilized trial, a revision trial, or other surface trial configuration, per the surgeon's preference.

The other bearing surface trial 192 shown in FIG. 6 is embodied as a mobile bearing surface trial component. The term "mobile bearing surface trial component" as used herein refers to a bearing surface trial component that is permitted to rotate relative to the tibial base trial component 14 when the bearing surface trial and the shim are attached thereto (i.e., it is configured to substantially rotate or move in the anterior-posterior direction or the medial-lateral direction relative to the tibial base trial component 14). The mobile bearing surface trial component may be embodied as a cruciate retaining trial, a posterior stabilized trial, a revision trial, or other surface trial configuration, per the surgeon's preference. Liked the fixed version, in embodiments where the mobile bearing surface trial component is embodied as a posterior stabilized trial, the mobile bearing surface trial component may include a spine extending upwardly from the upper bearing surface thereof.

The surgeon may assemble one of the shims 190 with one of the bearing surface trial components 192 to form a tibial bearing trial component 20. For example, the surgeon may select one of the fixed bearing surface trial components 192 and secure the shim 190 thereto to form a fixed bearing trial component 20. During a surgical trialing procedure, the fixed bearing trial component is advanced such that the anti-rotation lug 120 is received in a slot 232 of the shim 190 and the central post 94 is received in a central passageway 222 of the shim. The inner walls of the shim 190 cooperate with the anti-rotation lug 120 to prevent the fixed bearing trial component from rotating relative to the base trial component 14.

Alternatively, the surgeon may assemble one of the shims 190 with one of the mobile bearing surface trial components 192 to form a mobile bearing trial component 20. During a surgical trialing procedure, the mobile bearing trial component is advanced such that the anti-rotation lug 120 is received in the slot 234 of the shim 190 and the central post 94 is received in the central passageway 222 of the shim. The size and arcuate shape of the slot 234 of the shim 190 permits the mobile bearing trial component to rotate relative to the base trial component 14. When the mobile bearing trial component is rotated in one direction, the anti-rotation lug 120 acts as a stop to permit rotation of a defined distance such as, for example, approximately fifty degrees.

Referring now FIGS. 7-11, the system 10 further includes a keel punch 22. The keel punch 22 is configured to be inserted through the plate opening 38 of the base trial component 14 into the proximal end 604 of the patient's tibia 606 to prepare the patient's tibia 606 for a prosthetic component. The keel punch 22 has a base plate 78 having a peripheral rim 82 defined therein. The base plate 78 of the keel punch 22 has a configuration similar to the base plate 78 of the tibial evaluation components 16. As such, like reference numerals are utilized in the description of the keep punch 22 to describe features that are similar to those features already discussed in regard to the tibial evaluation components 16. The rim 82 of the keel punch's base plate 78 has an inferior surface 84 configured to engage the shelf surface 52 of the base trial component 14 when the keel punch 22 is seated on the base trial component 14. The base plate 78 of the keel punch 22 also includes a central platform 86 sized to be received in the central opening 40 of the base trial component 14, along with a pair of prongs 88, 90 that extend outwardly from the central platform 86. The prongs 88, 90 are sized to be received in the elongated openings 42 of the base trial component 14.

As can be seen in FIGS. 7-11, the central post 94 of the keel punch 22 is identical to the central post 94 of the tibial evaluation component 16. As such, the flange 100 of the post's connector 98 has a ramp surface 102 defined therein, with a ramp surface 116 also being defined in the post's anti-rotation lug 120. Ramp surfaces 124 are also defined in each of the post's collars 122. In a similar manner to as described above in regard to the tibial evaluation component 16, such ramp surfaces facilitate installation of the tibial bearing trial component 20 to the keel punch 22.

Figure 7:
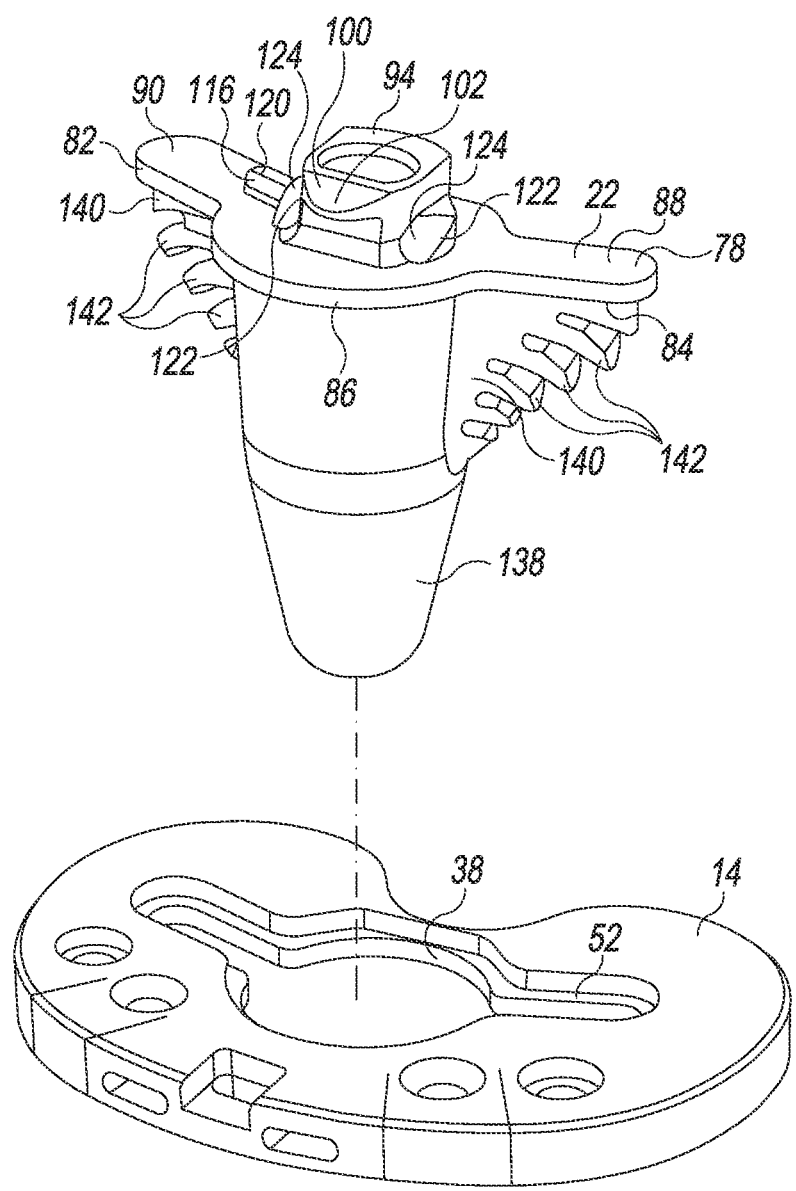
FIG. 7 is an exploded perspective view of a keel punch used with the tibial base trial component of the orthopaedic surgical instrument system of FIG. 1.
Figure 8:
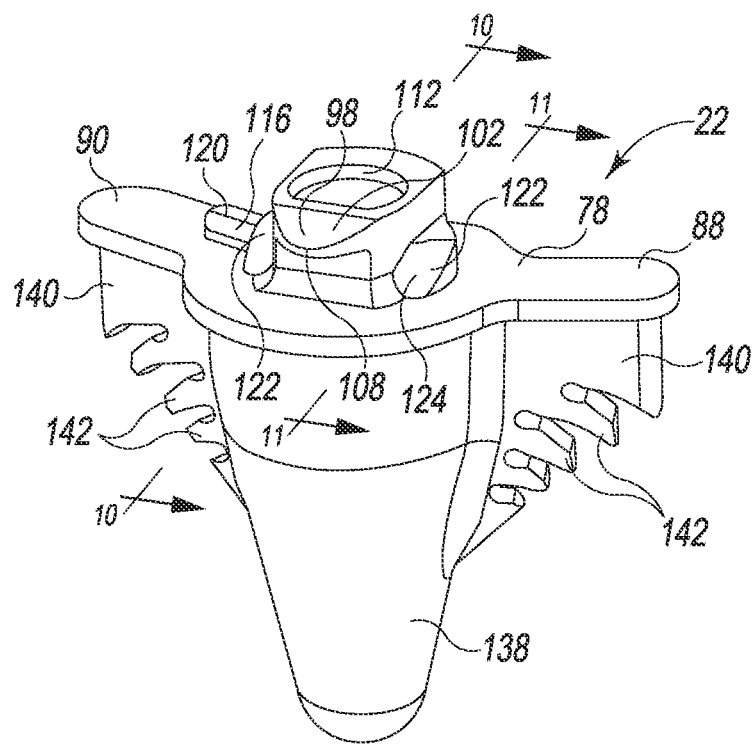
FIG. 8 is a perspective view of the keel punch of FIG. 7.
Figure 9:
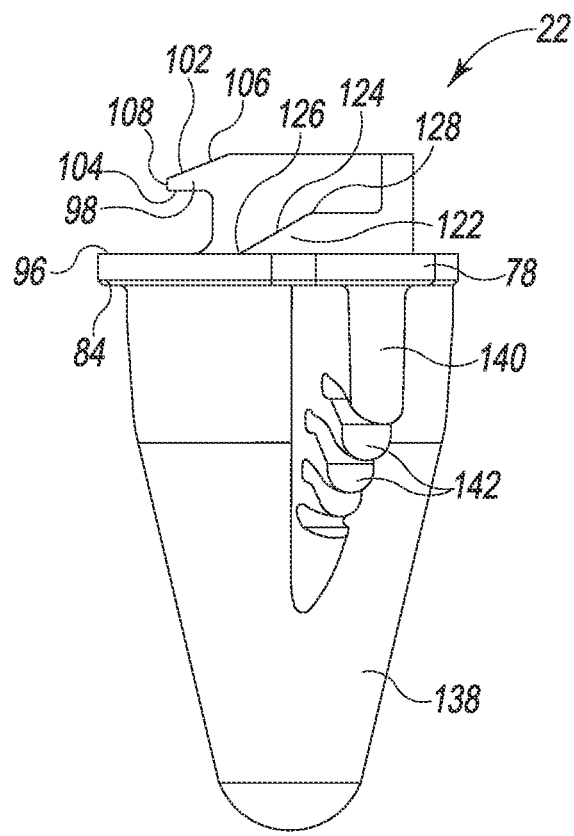
FIG. 9 is a side elevation view of the keel punch of FIG. 8.
Figure 10:
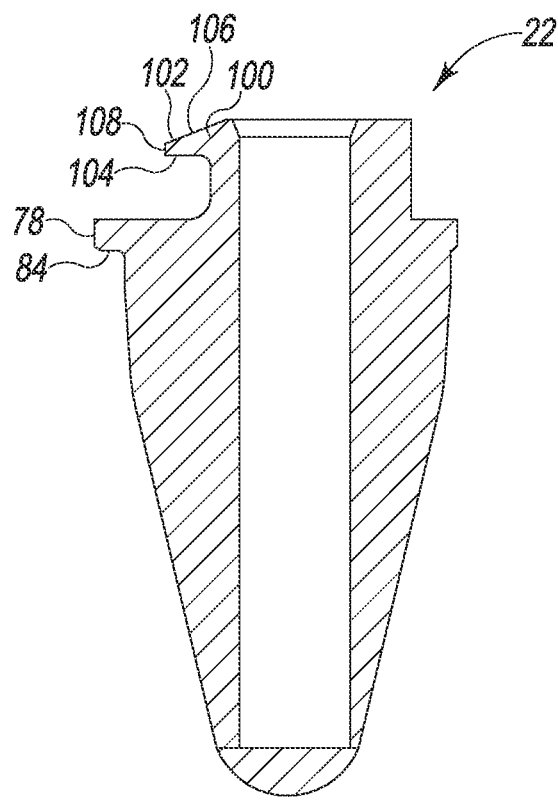
FIG. 10 is a cross sectional view of the keel punch taken along the line 10-10 of FIG. 8, as viewed in the direction of the arrows.
Figure 11:
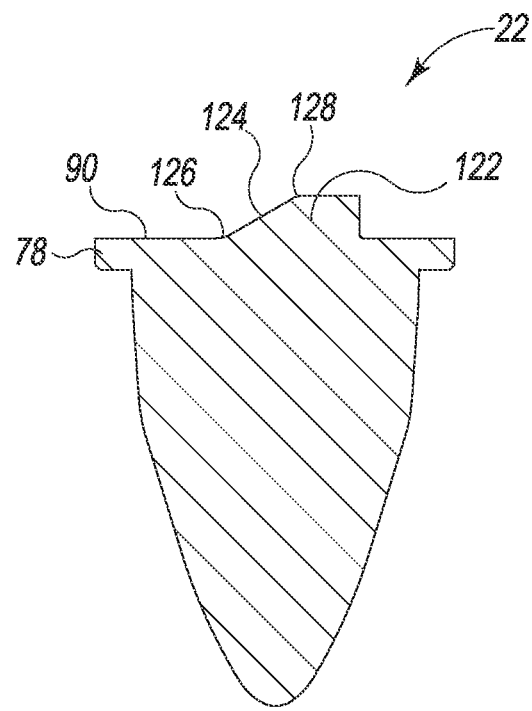
FIG. 11 is a cross sectional view of the keel punch taken along the line 11-11 of FIG. 8, as viewed in the direction of the arrows.

As can be seen in FIGS. 7 and 8, a tapered cylindrical post or bullet 138 extends inferiorly from the inferior surface of the keel punch's base plate 78. A pair of serrated wings 140 extend outwardly away from the bullet 138. One of the serrated wings 140 extends medially from the medial side of the bullet 138, with the other serrated wing extending laterally from the lateral side of the bullet 138. The bullet 138 has circular cross section that varies in diameter along its length (i.e., the diameter of the bullet 138 tapers in the superior-inferior direction). In that way, the cross sectional diameter of the bullet 138 at an upper end is greater than the cross sectional diameter of the bullet 138 at its lower end (i.e., its tip). A number of downwardly extending teeth 142 are defined in each of the serrated wings 140. The teeth 142 are configured to engage the patient's tibia 606 to define an opening in the proximal end 604 of the patient's tibia 606 sized to receive a tibial implant.

As described above, the system 10 also includes the guide tower 24 (see FIG. 14), which is configured to be positioned on the base trial component 14 during use. One example of a guide tower is shown and described in U.S. patent application Ser. No. 13/530,952, now U.S. Pat. No. 8,852,197, entitled "SURGICAL INSTRUMENT ASSEMBLIES FOR USE IN SURGICALLY PREPARING A TIBIA FOR IMPLANTATION OF A PROSTHETIC COMPONENT" by David Waite et al., which is incorporated herein by reference. The guide tower 24 is used by a surgeon to align and guide advancement of the keel punch 22 into the patient's tibia 606.

Referring now to FIGS. 12-15, portions of an orthopaedic surgical procedure utilizing the system 10 is shown. The surgeon first performs a resection of the distal end 600 of the patient's femur 602 and a resection of the proximal end 604 of the patient's tibia 606 to surgically prepare those ends for trial reduction. For example, the surgically-prepared proximal end 604 of the patient's tibia 606 also includes a resected surface 614 configured to receive the tibial base trial component 14.

The surgeon then performs an initial trial reduction. In doing so, the surgeon uses the system 10 to evaluate and check the stability and kinematics of the patient's femur 602 and tibia 606 for implantation of a fixed bearing knee prosthesis or a mobile bearing knee prosthesis. In the trial reduction process, the surgeon installs the femoral trial component 18 on the distal end 600 of the patient's femur 602, as shown in FIG. 13.

Figure 12:
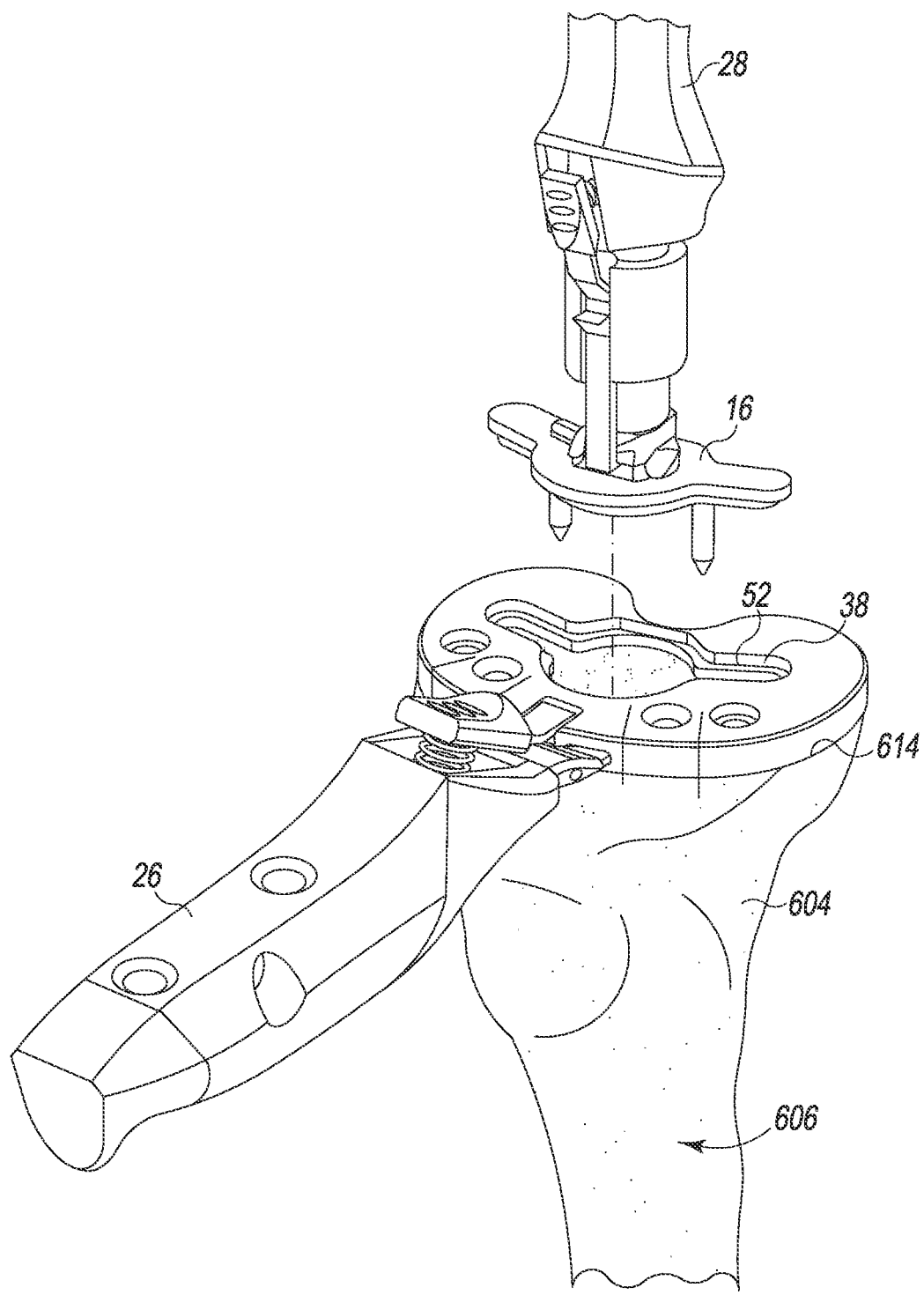
FIGS. 12-15 are views of a patient's femur, tibia, and the orthopaedic surgical instrument system of FIGS. 1-11 as the orthopaedic surgical instrument system is used in the performance of a surgical procedure to implant a knee prosthesis.

As shown in FIG. 12, the surgeon also positions the tibial base trial component 14 on the resected surface 614 of the patient's tibia 606. The surgeon may then select one of the tibial evaluation components 16 to be placed in the plate opening 38 of the base trial component 14. If the surgeon desires a fixed bearing trial component, the surgeon may select a spikeless tibial evaluation component 16 and position it in the plate opening 38 by hand so that the inferior surface 84 of the component's rim 82 engages the shelf surface 52 of the base trial component 14. If the surgeon desires a mobile bearing trial component, the surgeon may select a spiked tibial evaluation component 16, as shown in FIG. 12.

To position the spiked tibial evaluation component 16 in the plate opening 38 of the base trial component 14, the surgeon may attach the tibial evaluation component 16 to the impaction handle 28. The tibial evaluation component 16 and impaction handle 28 are then positioned over the plate opening 38, and the surgeon may then apply force to the handle 28 to tap the tibial evaluation component 16 into the proximal end 604 of the patient's tibia 606. In doing so, the spikes 130 extending from the prongs 88, 90 of the tibial evaluation component 16 are driven into the proximal end 604 of the patient's tibia 606. The surgeon continues driving the tibial evaluation component 16 into the patient's tibia 606 until the inferior surface 84 of component's rim 82 engages the shelf surface 52 of the tibial base trial component 14.

Once the selected tibial evaluation component 16 (i.e., spiked or spikeless) is properly seated, the surgeon may select a trial shim 190 and a tibial bearing surface trial component 192. If the surgeon desires a fixed bearing trial component, a fixed bearing surface trial component 192 may be selected and attached to one of the trial shims 190.

Figure 18:
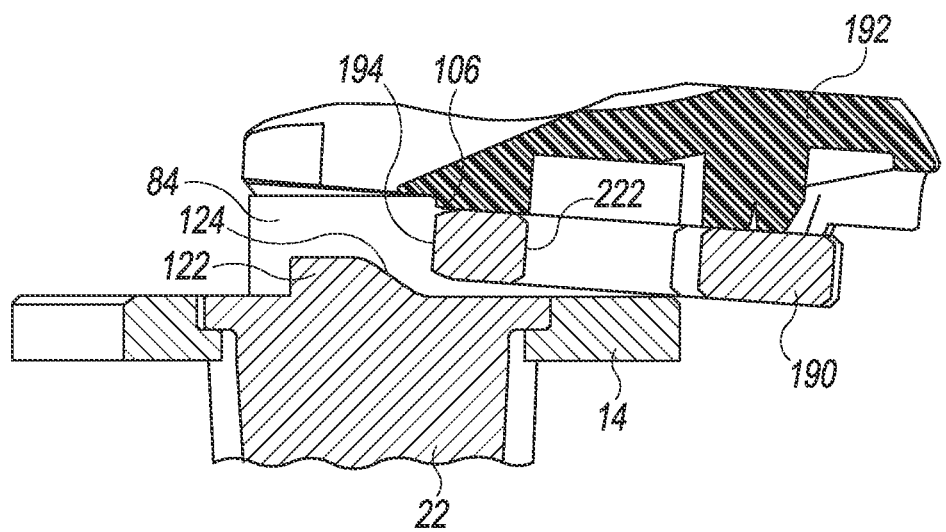
Figure 19:
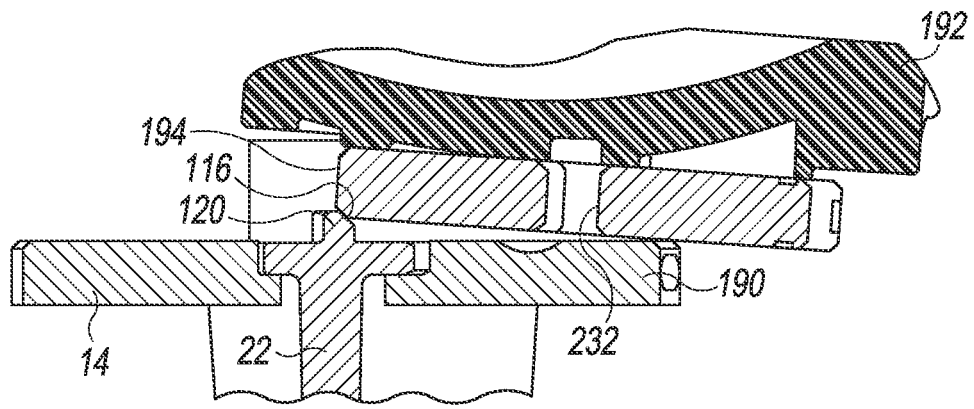
Figure 20:
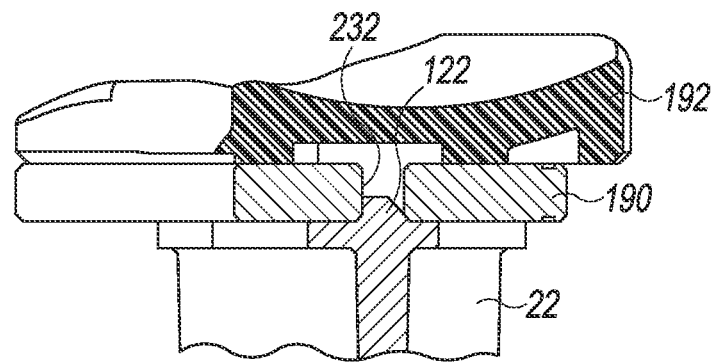

The surgeon then advances the posterior edge of the assembled tibial bearing surface trial component 192 and shim 190 into the gap between the tibial base trial component 14 and the femoral trial component 18. As can be seen in the progressive motion views of FIGS. 16-20, as the posterior/leading edge 194 of the tibial bearing surface trial component 192 and the posterior/leading edge 194 of the shim 190 are moved in the anterior-to-posterior direction, the leading edges 194 contact the ramp surfaces 102, 116, 124 of the tibial evaluation component's central post 94 and ride up the ramp surfaces 102, 116, 124. As the leading edges of the tibial bearing surface trial component 192 and the shim 190 ride up the ramp surfaces 102, 116, 124 of the tibial evaluation component's central post 94, the posterior edge of the tibial bearing surface trial component 192 is urged superiorly in a direction away from the tibial base trial component 14 thereby likewise urging the femoral trial component 18 superiorly in a direction away from the tibial base trial component 14 (see FIGS. 18 and 19). This increases the size of the gap between tibial base trial component 14 and the femoral trial component 18 so as to allow the assembled tibial bearing surface trial component 192 and shim 190 to be slipped therebetween with little to no subluxation of the patient's tibia 606. As shown in FIG. 20, once the leading edge of the slot 232 formed in the shim 190 clears the trailing edge of the anti-rotation lug 120, the shim 190 (and hence the tibial bearing surface trial component 192 secured thereto) snaps down into a position in which the anti-rotation lug 120 is received in a slot 232 of the shim 190 and the central post 94 is received in a central passageway 222 of the shim.

As shown in FIG. 13, when the fixed bearing trial component 20 is in place, the surgeon carefully extends the knee of the patient, noting the anteroposterior stability, medial-lateral stability, and overall alignment in the anterior-posterior ("A/P") plane and medial-lateral ("M/L") plane. Rotational alignment of the tibial base trial component 14 may be adjusted with the knee in full extension, using the handle 26 to rotate the trial 14 and the bearing trial component 20 relative to the femoral trial component 18. The rotation of the base trial component 14 is usually centered on the junction between the medial and central one-third of the tibial tubercle.

As the range of motion is evaluated, the load on the femoral trial component 18 translates posteriorly as the knee is moved between extension and flexion. To improve performance, the surgeon may remove the fixed bearing trial component 20 from the tibial base trial component 14 to exchange the shim 190 and/or the bearing surface trial component 192. A removal tool (not shown) may be used to detach the fixed bearing trial component 20 from the base trial component 14. The surgeon may use a separator tool (not shown) to detach the shim 190 from the fixed bearing surface trial component 192. The surgeon may then select another shim 190 having a different thickness or choose a fixed bearing surface trial component 192 with an alternative configuration, such as, for example, a fixed bearing surface trial component 192 that is cruciate retaining or posterior stabilized. In some cases, the surgeon may switch to a mobile bearing surface trial component 192. The surgeon may continue to try various combinations of shims 190 and bearing surface trial components 192 to ascertain which final implant will have the best stability in flexion and extension while permitting full extension. Once the revised combination of a shim 190 and bearing surface trial component 192 is selected, the two components are assembled to one another and anteriorly advanced in the gap between tibial base trial component 14 and the femoral trial component 18 in the manner previously discussed.

If the surgeon desires instead a mobile bearing trial component 20, a mobile bearing surface trial component 192 may be selected and attached to one of the trial shims 190. The surgeon then advances the posterior edge of the assembled tibial bearing surface trial component 192 and shim 190 into the gap between the base trial component 14 and the femoral trial 18 in the same manner as described above in regard to the fixed bearing trial component 20. As can be seen in the progressive motion views of FIGS. 16-20, as the posterior/leading edge 194 of the tibial bearing surface trial component 192 and the posterior/leading edge 194 of the shim 190 are moved in the anterior-to-posterior direction, the leading edges contact the ramp surfaces 102, 116, 124 of the tibial evaluation component's central post 94 and ride up the ramp surfaces 102, 116, 124. As the leading edges of the tibial bearing surface trial component 192 and the shim 190 ride up the ramp surfaces 102, 116, 124 of the tibial evaluation component's central post 94, the posterior edge of the tibial bearing surface trial component 192 is urged superiorly in a direction away from the tibial base trial component 14 thereby likewise urging the femoral trial component 18 superiorly in a direction away from the tibial base trial component 14 (see FIGS. 18 and 19). This increases the size of the gap between tibial base trial component 14 and the femoral trial component 18 so as to allow the assembled tibial bearing surface trial component 192 and shim 190 to be slipped therebetween with little to no subluxation of the patient's tibia 606. Once the leading edge of the arcuate slot 234 formed in the shim 190 clears the trailing edge of the anti-rotation lug 120, the shim 190 (and hence the tibial bearing surface trial component 192 secured thereto) snaps down into a position in which the anti-rotation lug 120 is received in the slot 234 of the shim 190 and the central post 94 is received in a central passageway 222 of the shim. As described above, the size and arcuate shape of the slot 234 of the shim 190 permits the mobile bearing trial component 20 to rotate relative to the base trial component 14. When the mobile bearing trial component 20 is rotated in one direction, the anti-rotation lug 120 acts as a stop to permit rotation of a defined distance such as, for example, approximately fifty degrees.

With the femoral trial component 18, the tibial base trial component 14, and the mobile bearing trial component 20 in place, the surgeon may extend the knee and note the anteroposterior stability, medial-lateral stability, and overall alignment in the A/P and M/L planes. The surgeon is also able to assess the bearing rotation and patellofemoral tracking because the mobile bearing trial component 20 is rotatable about the base trial component 14.

Once the surgeon is satisfied with the trial reduction, the tibial trial component 20 and the tibial evaluation component 16 are removed from the tibial base trial component 14.

Figure 14:
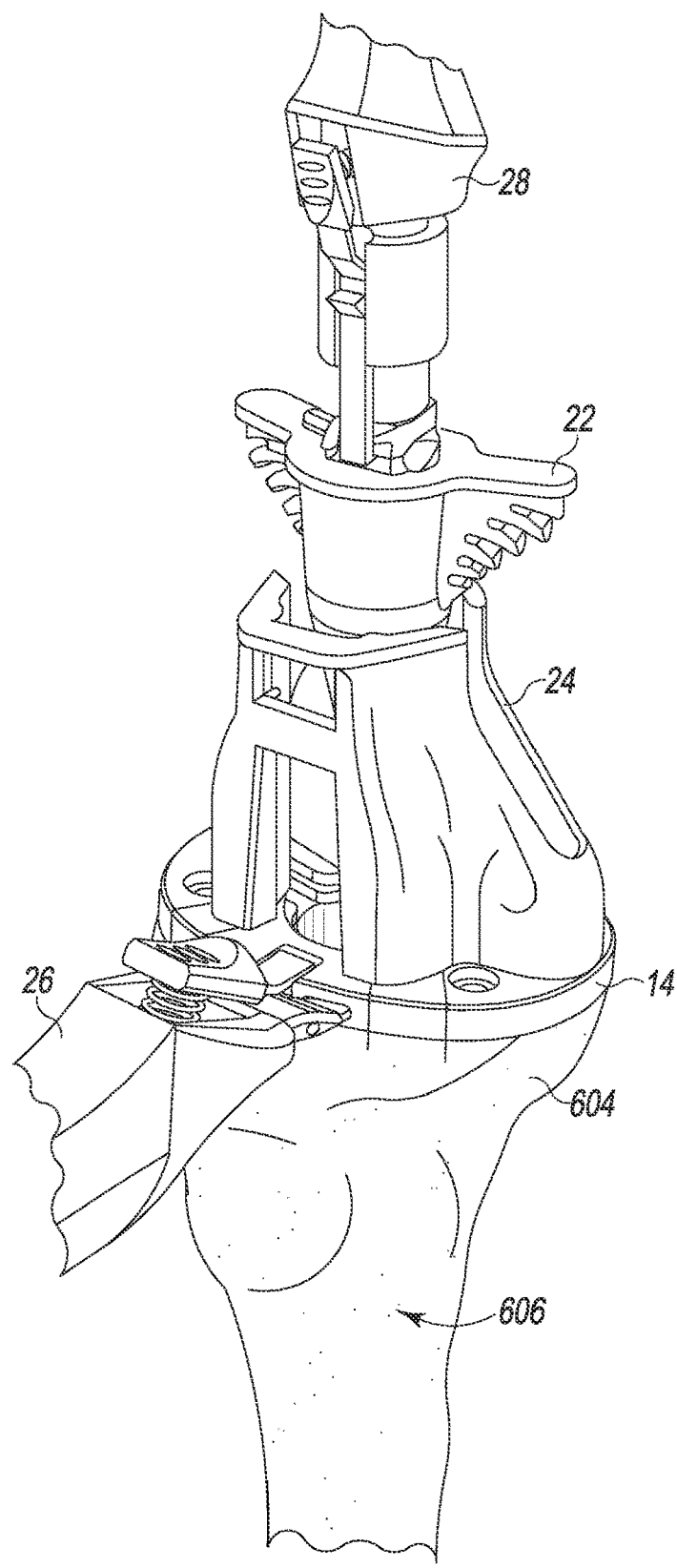

Referring now to FIG. 14, after performance of the trial reduction, the surgeon then continues surgical preparation of the proximal end 604 of the patient's tibia 606. Specifically, the guide tower 24 is positioned on tibial base trial component 14 so that its fixation pins (not shown) extend through the designated holes of the tibial base trial component 14 and into the proximal end 604 of the patient's tibia 606. The surgeon may then use the base trial component 14 and the tower 24 as a guide to surgically ream the proximal end 604 of the patient's tibia 606. Thereafter, as shown in FIG. 14, the keel punch 22 is impacted into the proximal end 604 of the patient's tibia 606 using the impaction handle 28 before the guide tower 24 is removed. An exemplary procedure for reaming the patient's tibia 606 and installing the keel punch 22 is set forth in U.S. patent application Ser. No. 13/530,945, now U.S. Pat. No. 8,926,619, entitled "METHOD OF SURGICALLY PREPARING A TIBIA FOR IMPLANTATION OF A PROSTHETIC COMPONENT" filed by David Waite et al. and filed on Jun. 22, 2012, which is incorporated herein by reference.

Figure 15:
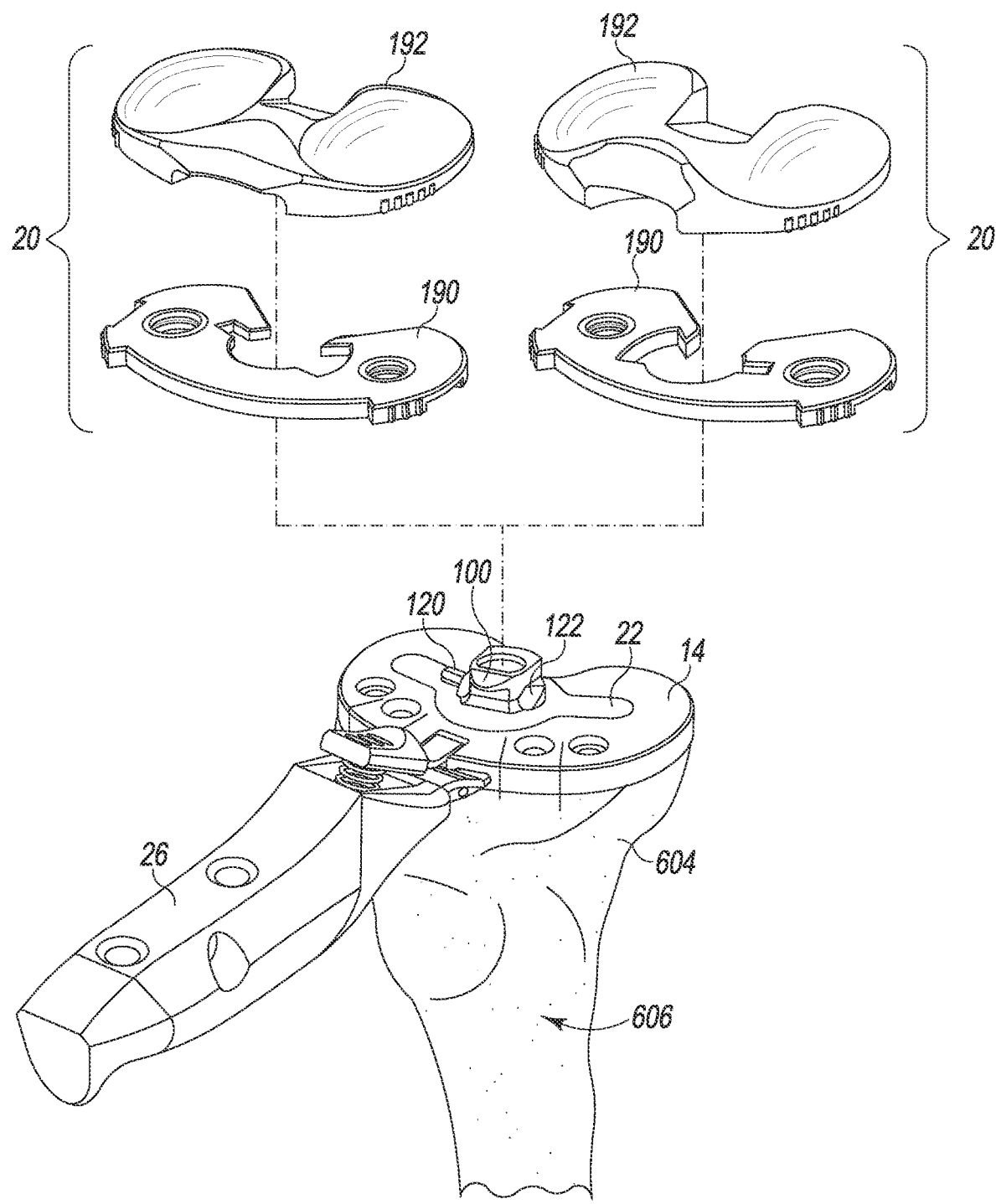
Figure 16:
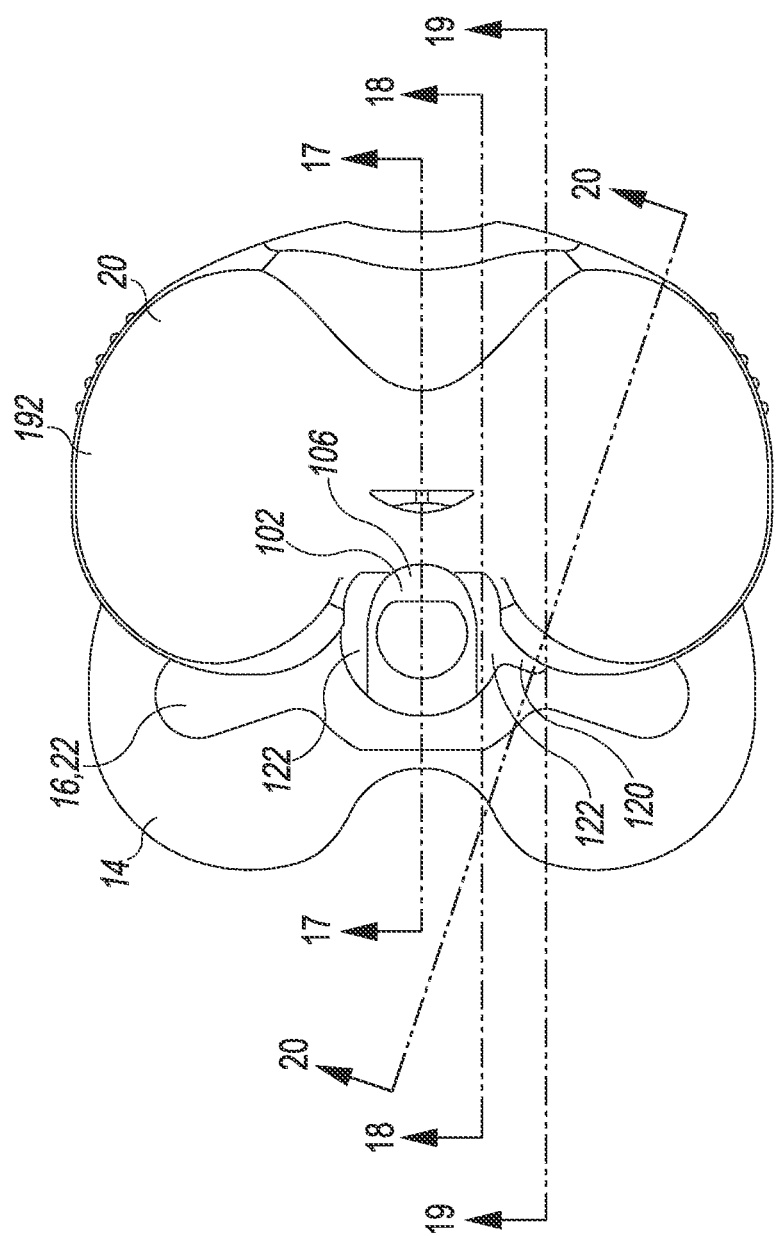
FIG. 16 is a top elevation view showing the tibial bearing trial component of the of the orthopaedic surgical instrument system being advanced onto either the tibial evaluation component or the keel punch.
Figure 17:
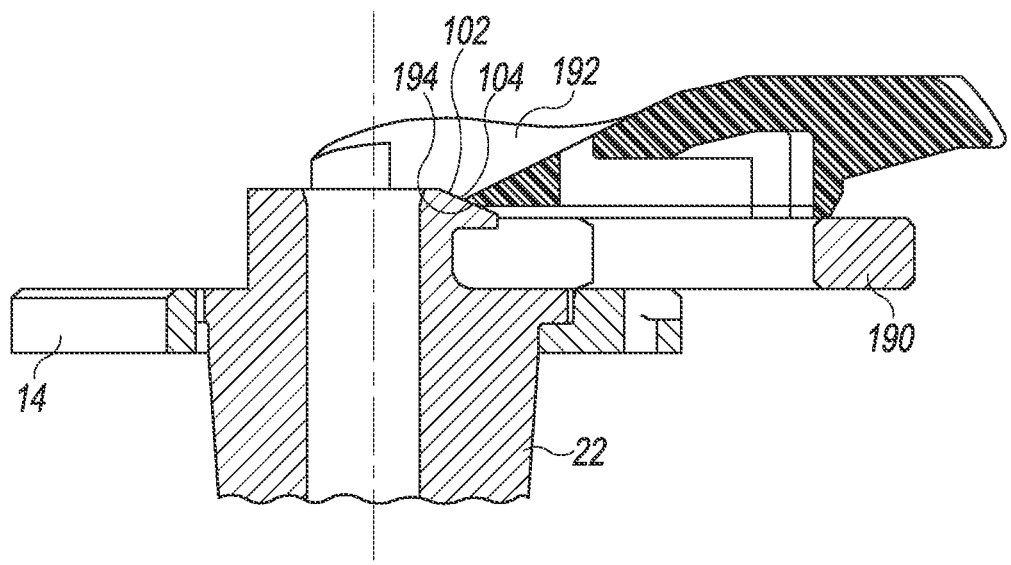
FIGS. 17-20 are cross sectional views taken along their respective lines of FIG. 16 (as viewed in the direction of the arrows) showing the tibial bearing trial component during various stages of anterior advancement onto either the tibial evaluation component or the keel punch.

Subsequently, the surgeon determines whether any additional trial reduction is necessary. If so, the surgeon may utilize the keel punch 22 seated on the tibial base trial component 14 in the proximal end 604 of the patient's tibia 606 to perform an additional trial reduction. As shown in FIG. 15, the surgeon may assemble a fixed bearing trial component 20 or a mobile bearing trial component 20 and anteriorly advance the trial component 20 into the gap between tibial base trial component 14 and the femoral trial component 18 and over the central post 94 and the antirotation lug 120 of the keel punch 22 in the same manner as described above in regard to the tibial evaluation component 16 with little to no subluxation of the patient's tibia 606. The surgeon may then repeat the trial reduction until satisfied with the alignment and the stability of the knee.

When the additional trial reduction is complete, the surgeon may use the impaction handle 28 to remove the keel punch 22 from the patient's tibia 606. The resultant features surgically formed in the proximal end 604 of the patient's tibia 606 are configured to receive a tibial tray of a fixed bearing knee prosthesis or a mobile bearing knee prosthesis. The surgeon then completes the surgical procedure of the remaining components of the prosthesis.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument system for use during a surgical procedure to implant an orthopaedic knee prosthesis, comprising:
   a tibial trial component configured to be positioned on a surgically-prepared proximal end of a patient's tibia, the tibial trial component having a base plate and a central post extending upwardly from a superior surface of the base plate, wherein a superior surface of the central post has a ramp surface defined therein, the ramp surface inclines superiorly in an anterior-to-posterior direction.

2. The orthopaedic surgical system of claim 1, wherein:
   the central post comprises a collar extending outwardly from a longitudinal axis of the central post, and
   a ramp surface is defined in a superior surface of the collar.

3. The orthopaedic surgical system of claim 2, wherein: the ramp surface defined in the collar has an anterior end and a posterior end,
   the anterior end of the ramp surface defined in the collar is coplanar with the superior surface of the base plate, and
   the posterior end of the ramp surface defined in the collar is spaced apart superiorly from the superior surface of the base plate.

4. The orthopaedic surgical system of claim 1, wherein:
   the central post comprises a connector configured to be secured to a surgical handle,
   the connector comprising a flange extending anteriorly away from a longitudinal axis of the central post, and
   the ramp surface defined in the central post is defined in a superior surface of the flange of the connector.

5. The orthopaedic surgical system of claim 1, wherein:
   the central post further comprises an elongated antirotation lug extending in a direction away from a longitudinal axis of the central post, and
   the ramp surface defined in the central post is defined in a superior surface of the elongated anti-rotation lug.

6. An orthopaedic surgical instrument system for use during a surgical procedure to implant an orthopaedic knee prosthesis, comprising:
   a tibial trial component configured to be positioned on a surgically-prepared proximal end of a patient's tibia, the tibial trial component having a base plate and a central post extending upwardly from a superior surface of the base plate, wherein a superior surface of the central post has a ramp surface defined therein, the ramp surface inclines superiorly in an anterior-to-posterior direction, and
   a bearing trial component having an opening defined therein, the central post of the tibial trial component being configured to be received in the opening of the bearing trial component.

7. The orthopaedic surgical system of claim 6, wherein:
   the central post comprises a collar extending outwardly from a longitudinal axis of the central post, and
   a ramp surface is defined in a superior surface of the collar.

8. The orthopaedic surgical system of claim 7, wherein:
   the ramp surface defined in the collar has an anterior end and a posterior end,
   the anterior end of the ramp surface defined in the collar is coplanar with the superior surface of the base plate, and
   the posterior end of the ramp surface defined in the collar is spaced apart superiorly from the superior surface of the base plate.

9. The orthopaedic surgical system of claim 6, wherein the bearing trial component comprises:
   a tibial bearing surface trial component having an articular surface, and
   a shim removably secured to the tibial bearing surface trial component.

10. The orthopaedic surgical system of claim 6, wherein:
    the central post comprises a connector configured to be secured to a surgical handle,
    the connector comprising a flange extending anteriorly away from a longitudinal axis of the central post, and
    the ramp surface defined in the central post is defined in a superior surface of the flange of the connector.

11. The orthopaedic surgical system of claim 6, wherein:
    the central post further comprises an elongated antirotation lug extending in a direction away from a longitudinal axis of the central post, and the ramp surface defined in the central post is defined in a superior surface of the elongated anti-rotation lug.

* * * * *